(12) United States Patent
Wainright et al.

(10) Patent No.: US 6,306,273 B1
(45) Date of Patent: Oct. 23, 2001

(54) METHODS AND COMPOSITIONS FOR CONDUCTING PROCESSES IN MICROFLUIDIC DEVICES

(75) Inventors: Ann K. Wainright, Cupertino; Irene Visser, San Ramon; Sharat Singh, San Jose, all of CA (US)

(73) Assignee: Aclara BioSciences, Inc., Mountain View, CA (US)

( * ) Notice: Subject to any disclaimer, the term of this patent is extended or adjusted under 35 U.S.C. 154(b) by 0 days.

(21) Appl. No.: 09/291,169

(22) Filed: Apr. 13, 1999

(51) Int. Cl.$^7$ .......................... G01N 27/26; G01N 27/447
(52) U.S. Cl. .......................... 204/454; 204/450; 204/451; 204/600; 204/601
(58) Field of Search .................................... 204/450, 451, 204/452, 453, 454, 455, 600, 601, 602, 603, 604, 605

(56) References Cited

U.S. PATENT DOCUMENTS

| | | | |
|---|---|---|---|
| 4,518,701 | * 5/1985 | Khanna et al. | 436/500 |
| 4,591,638 | * 5/1986 | Ahrgren et al. | 536/51 |
| 4,621,048 | * 11/1986 | Ashihara et al. | 435/5 |
| 4,824,776 | * 4/1989 | Heller | 435/6 |
| 5,015,350 | 5/1991 | Wiktorowicz | 204/454 |
| 5,223,338 | * 6/1993 | Malhotra | 428/342 |
| 5,244,714 | * 9/1993 | Malhotra et al. | 428/195 |
| 5,246,867 | * 9/1993 | Lakowicz et al. | 436/95 |
| 5,259,939 | 11/1993 | Chen | 204/451 |
| 5,264,101 | * 11/1993 | Demorest et al. | 204/452 |
| 5,391,274 | 2/1995 | Shieh | 204/454 |
| 5,397,852 | * 3/1995 | Edwards et al. | 549/221 |
| 5,545,302 | * 8/1996 | Zhu et al. | 204/454 |
| 5,611,903 | 3/1997 | Janssens et al. | 204/454 |
| 5,627,078 | * 5/1997 | Karl et al. | 436/512 |
| 5,766,435 | 6/1998 | Liao et al. | 204/451 |
| 6,042,710 | * 3/2000 | Dubrow | 204/454 |

FOREIGN PATENT DOCUMENTS

| | | |
|---|---|---|
| 0 665 430 A1 | 8/1995 | (EP) . |
| WO98/00709 | 1/1998 | (WO) . |
| WO 98/45929 | 10/1998 | (WO) . |

OTHER PUBLICATIONS

Morgan Stefansson et al, "Aminodextrari as a Migration Moderator in capillary Gel Electrophoresis of Charged Polysacchrides", Analytical Chemistry, vol. 69, No. 18, pp. 3846–3850, Sep. 15, 1997.*
Capellil et al. (1996) *J. Biochem Biophys Methods* 14:32(2), 109–24.
Corradini et al. (1995) *Electrophoresis* 16:630–35.
Girault et al. (1997) *Anal. Chem.* 69:2035–42.
Harrison et al. (1997) *Anal. Chem.* 69:1564–68.
Harrison et al. (1998) *Clin. Chem.* 44(3):591–98.
Hjerten et al. (1993) *Eletrophoresis* 14 (5–6):390–96.
*J. Microcolumn Separation* (1997) 9:1–7.
Katayama et al. (1998) *Anal. Chem.* 70:2254–60.
Li et al. (1994) *J. Chromatogr.* 680:431–35.
Novotny et al. (1995) *Electrophoresis* 16:396–401.
Ramsey et al. (1997) *Anal. Chem.* 69:3407–12.
Rassi et al. (1993) *Electrophoresis* 14:396–406.
Regneir et al. (1990) *J. Chromatogr.* 516:69–78.
Regneir et al. (1992) *J. Chromatography* 608:217–24.
Regneir et al. (1993) *Anal Chem.* 65:2029–35.
Regneir et al. (1993) *Anal Chem.* 65:2655–62.
Regneir et al. (1993) *Anal Chem.* 65:3267–3270.
Whitesides et al. (1992) *J. Med. Chem.* 35:2915–17.
Whitesides et al. (1993) *J. Med. Chem.* 36:126–133.
Whitesides et al. (1993). *J. Org. Chem.* 58:5508–12.
Whitesides et al. (1997) *Anal. Chem.* 69(7):1370–79.
Wiktorowicz et al. (1990) *Electrophoresis* 11:769–773.

* cited by examiner

*Primary Examiner*—Jill Warden
*Assistant Examiner*—John S. Starsiak, Jr.
(74) *Attorney, Agent, or Firm*—Perkins Coie LLP

(57) ABSTRACT

A method is disclosed for controlling the direction and transport of a material on a microfluidic device formed from an acrylic polymer, by electrokinetic flow of a fluid containing the material. The method comprises providing an electrokinesis buffer containing a charged hydrophilic polymer, wherein charges on the polymer are randomly distributed. The method has applications for improved transport of proteins and transport of materials comprising differentially charged chemical species. A preferred embodiment of the present invention comprises use of the disclosed method for electrokinetic separations of a mixture of polypeptides having both positive and negative charges. Another preferred embodiment concerns use of the disclosed method for performing an assay involving mixing of two or more reagents, wherein a first reagent comprises an enzyme and a second reagent comprises species having an opposite charge to the enzyme.

7 Claims, 10 Drawing Sheets

SEQUENCE LISTING

<160> NUMBER OF SEQ ID NOS: 3

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: labeled
      artificial peptide with specific ratio of lysines and alanines to
      achieve defined charge/mass ratio
<221> NAME/KEY: MOD_RES
<222> LOCATION: (1)
<223> OTHER INFORMATION: N-terminal amino acid linked to fluorescein
      isothiocyanate

<400> SEQUENCE: 1

Lys Lys Ala Ala
  1

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: labeled
      artificial peptide with specific ratio of lysines and alanines to
      achieve defined charge/mass ratio
<221> NAME/KEY: MOD_RES
<222> LOCATION: (1)
<223> OTHER INFORMATION: N-terminal amino acid linked to fluorescein
      isothiocyanate

<400> SEQUENCE: 2

Lys Lys Lys Ala
  1

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: labeled
      artificial peptide with specific ratio of lysines and alanines to
      achieve defined charge/mass ratio
<221> NAME/KEY: MOD_RES
<222> LOCATION: (1)
<223> OTHER INFORMATION: N-terminal amino acid linked to fluorescein
      isothiocyanate

<400> SEQUENCE: 3

Lys Lys Lys Lys

METHODS AND COMPOSITIONS FOR CONDUCTING PROCESSES IN MICROFLUIDIC DEVICES

BACKGROUND OF THE INVENTION

1. Field of the Invention

This invention relates generally to the processing of samples such as in the field of separation of biomolecules such as proteins and, in particular, separations by capillary electrophoresis and the use of capillary electrophoresis to detect such biomolecules and in the field of assays in general.

In a range of technology-based business sectors, including the chemical, bioscience, biomedical, and pharmaceutical industries, it has become increasingly desirable to develop capabilities for rapidly and reliably carrying out chemical and biochemical reactions in large numbers using small quantities of samples and reagents. Carrying out a massive screening program manually, for example, can be exceedingly time-consuming, and may be entirely impracticable where only a very small quantity of a key sample or component of the analysis is available, or where a component is very costly.

Accordingly, considerable resources have been directed to developing methods for high-throughput chemical synthesis, screening, and analysis. Subsequently, considerable art has emerged, in part, from such efforts. Automated laboratory workstations have contributed significantly to advances in pharmaceutical drug discovery and genomics over the past decade. See for example, U.S. Pat. Nos. 5,104,621 and 5,356,525 (Beckman Instruments). More specifically, robotics technology has played a major role in providing a practical useful means for enabling high throughput screening (AS) methods. Reference can be made to U.S. Pat. No. 4,965,049. Highly parallel and automated methods for DNA synthesis and sequencing have also contributed significantly to the success of the human genome project to date.

Computerized data handling and analysis systems have also emerged with the commercial availability of high-throughput instrumentation for numerous life sciences research and development applications. Commercial software, including database and data management software, has become routine in order to efficiently handle the large amount of data being generated. Bioinformatics has emerged as an important field.

With the developments outlined above in molecular and cellular biology, combined with advancements in combinatorial chemistry, have come an exponential increase in the number of targets and compounds available for screening. In addition, many new genes and their expressed proteins will be identified by the Human Genome project and will therefore greatly expand the pool of new targets for drug discovery. Subsequently, an unprecedented interest has arisen in the development of more efficient ultra-high throughput methods and instrumentation for pharmaceutical and genomics screening applications.

In recent parallel technological developments, miniaturization of chemical analysis systems, employing semiconductor processing methods, including photolithography and other wafer fabrication techniques borrowed from the microelectronics industry, has attracted increasing attention and has progressed rapidly. The so-called "lab-chip" technology enables sample preparation and analysis to be carried out on-board microfluidic-based cassettes. Moving fluids through a network of interconnecting enclosed microchannels of capillary dimensions is possible using electrokinetic transport methods.

Application of microfluidics technology embodied in the form of analytical devices has many attractive features for pharmaceutical high throughput screening. Advantages of miniaturization include greatly increased throughput and reduced costs, in addition to low consumption of both sample and reagents and system portability. Implementation of these developments in microfluidics and laboratory automation holds great promise for contributing to advancements in life sciences research and development.

Capillary-based separations are widely used for analysis of a variety of analyte species. Numerous subtechniques, all based on electrokinetic-driven separations, have been developed. Capillary electrophoresis is one of the more popular of these techniques and can be considered to encompass a number of related separation techniques such as capillary zone electrophoresis, capillary gel electrophoresis, capillary isoelectric focusing, capillary isotachophoresis, and micellar electrokinetic chromatography. In the context used throughout this application, the phrase "capillary electrophoresis" is used to refer to any and all of the aforementioned electrokinetic separation subtechniques.

Microfluidic devices provide fluidic networks in which biochemical reactions, sample injections and separation of reaction products can be achieved. The application of high voltage to conductive fluids within these channels leads to electroosmotic and/or electrophoretic pumping, providing both mass transport and separation of components within the sample. In these microfluidic devices, fluid flow and reagent mixing is achieved using electrokinetic transport phenomena (electroosmotic and electrophoretic). Electrokinetic transport is controlled by regulating the applied potentials at the terminus of each channel of the microfluidic device. Within the channel network, cross intersections and mixing tees are used for valving and dispensing fluids with high volumetric reproducibility (0.5% RSD). The mixing tee can be used to mix proportionately two fluid streams in ratio from 0 to 100% from either stream simply by varying the relative field strengths in the two channels.

When capillary electrophoresis is carried out using a fluid electrophoretic medium, the medium itself may undergo bulk flow migration through the capillary tube toward one of the electrodes. This electroosmotic flow is due to a charge shielding effect produced at the capillary wall interface. In the case of standard fused silica capillary tubes, which carry negatively charged silane groups, the charge shielding produces a cylindrical "shell" of positively charged ions in the electrophoresis medium near the surface wall. This shell, in turn, causes the bulk flow medium to assume the character of a positively charged column of fluid and migrate toward the cathodic electrode at an electroosmotic flow rate.

In some instances a prerequisite for conducting assays on microfluidic devices is the ability to transport large proteins (positive and negatively charged), substrates, cofactors and inhibitors or test compounds. Electroosmotic pumping has to be used to transport reagents and samples. Therefore, control of the electroosmotic flow (EOF) and capillary wall chemistry is critical to the success of a microfluidic device. It is well recognized that EOF is essential to move oppositely charged molecules in a single run; for example EOF will be used to mix a lest compound (positively charged) with a negatively charged substrate of an enzyme.

Capillary surface modifications have been an area of active research since the introduction of capillary electrophoresis. This has been prompted by the fact that basic solutes and especially proteins undergo adsorption onto the surface of capillaries. The interaction of solute with the capillary wall leads to band-broadening and in some cases irreversible adsorption. There is an enormous amount of literature describing surface modification of capillary surfaces to separate proteins. The adsorption of proteins on the walls of capillaries is a common problem in the analysis of proteins by capillary electrophoresis. Buffer additives, non-covalent coating and covalent coating have been reported to decrease protein adsorption on the walls of capillaries. Covalent coatings are especially useful in protocols that require minimal concentration of organic materials in the electrokinesis buffer. Dynamic coating is more practical to use in studies, in which separation of analyte from buffer is not important such as, for example, analysis of an enzymatic reaction.

Coatings on capillaries can be classified into two groups, one in which the modifications on the surface inhibit EOF while in others the coatings are designed to retain a certain level of EOF.

2. Previous Disclosures

Wiktorowicz in U.S. Pat. No. 5,015,350 (1991) discloses a method for achieving desired electroosmotic flow characteristics in a capillary tube having charged surface groups. An electrolyte solution containing a compound effective to stably alter the charge of the tube walls is drawn into and through the tube while the electroosmotic flow rate in the tube is being monitored, until a desired electroosmotic flow rate is achieved. The method is reported to optimize electrophoretic separation of charged protein or nucleic acid species in a capillary tube and to produce capillary tubes with desired charge density properties. The compound forms a coating on the tube walls and the method is referred to as a flow-rate controlled surface charge coating or FCSC.

U.S. Pat. No. 5,611,903 (Janssens, et al.) discusses capillary electrophoresis method using initialized capillary and polyanion-containing buffer and chemical kit therefor. The initiator forms a first coating on the inner wall of the capillary and the polyanion in the buffer forms a second coating on the first coating. The polyanion is not in the electrophoresis buffer, which contains the sample to be analyzed.

Okafo, et al., describes effective ion pairing for the separation of basic proteins in capillary electrophoresis. A sodium salt of phytic acid (myoinositol hexakis-(dihydrogen phosphate) is added to the separation buffer.

Fu-Tai (U.S. Pat. No. 5,259,939, 1993) describes the use of zwitterionic salts in capillary electrophoresis to prevent protein adsorption to walls.

Hjerten, et al., (*Electrophoresis* 1993, 14(5–6):390–396) describes the use of methylcellulose and dextrans to coat fused silica capillaries to eliminate EOF and adsorption of proteins to the capillary walls.

Engelhardt, et al. (EP 0 665 430 A1), discuss a capillary made of plastics material for use in capillary electrophoresis and process for its production. In the modified capillary according to Engelhardt the functional groups can be chemically bonded to atoms of the base plastics material. The functional groups can be created from or are directly chemically bonded to sites of the base polymer capillary material which are created in addition to natural occurring active sites of the polymer. Preferably, the functional residues are predominately hydrophilic groups. In particular the functional groups can be hydroxyl groups. Also, in particular, the functional groups can be amino groups or ammonium groups. With particular advantage the functional groups can be of a type and be present in an amount adapted to effect a desired variation in electrokinetic behavior. Preferably, the functional groups are adapted to control the electroosmotic flow (EOF). In the modified polymer capillary according to Engelhardt, the functional groups can be non-ionic and/or ionic. The functional groups can be ionic with positive charge; also, the functional groups can be ionic with negative charge. The functional property of the inner surface of a capillary modified according to the invention is intended to be that proteins do at most only reversibly adhere; preferably, they do not at all adhere thereon.

U.S. Pat. No. 5,391,274 (Chia-Hui Shieh) discloses methods for controlling electroosmotic flow in coated capillary electrophoresis columns. The methods discussed involve varying the concentration of a multi-valent buffer compound in electroosmotic buffer in order to control the electroosmotic flow in capillary columns having interior surfaces coated with charged organic coatings.

Nikiforov, et al., disclose methods and systems for enhanced fluid transport in WO 98/45929. The methods generally comprise providing an effective concentration of at least one zwitterionic compound in the fluid containing the material that is to be transported or directed.

Whitesides, et al. (*Anal Chem.*1997, 69(7):1370–1379), Regneir, et al., *J. Chromatogr.* 1990, 516:69–78; Li, et al.,*J. Chromatogr.* 1994, 680:431–435 describe a method to limit adsorption of proteins based on the adsorption of positively charged polymers on the negatively charged inner surface of fused silica capillaries. The positively charged surface did not adsorb positively charged proteins but could promote adsorption of negatively charged proteins and compounds. Other workers in this area include Wiktorowicz, et al., *Electrooresis* 1990, 11:769–774; Katayama, et al., *Anal. Chem.* 1998, 70:2254–2260; Danillo Corradini, et al., *Electrophoresis* 1995, 16:630–635; Capellil, et al., *J. Biochem Biophys Methods* 1996, 14:32(2), 109–124).

One problem with the above approaches appears, based on our studies, to be that positively charged proteins can be moved by anodal EOF but that negatively charged substrates and cofactors can not be prevented from adsorbing to the modified capillary walls under optimum reaction conditions of kinase.

Rassi, et al. *Electrophoresis* 1993, 14:396–406) describes multiple covalent polyether coating on capillaries to achieve both switchable anodal and cathodal EOF.

Novotny, et al., (*Electrophoresis* 1995, 16:396–401) report a versatile, hydrolytically stable coating of fused silica capillaries with acrylamide and cellulose. These capillaries have low EOF and were used to separate peptides, glycoproteins, etc.

A. Fridstrom, et al., PCT WO98/00709 describe adsorbing phenyl dextran to polypropylene capillaries by hydrophobic association. They demonstrated that phenyl dextran modifies the polypropylene surface by making it more hydrophilic and increases the compatibility of polypropylene columns for proteins. A similar disclosure is found in *J. Microcolumn Separation* 1997, 9:1–7.

Regneir, et al. (*Anal Chem.* 1993, 6:2655–2662; 1993, 65:2029–2035; 1993, 65:3267–3270; *J. Chromatography* 1992, 608:217–224) describe a concept in reaction based chemical analysis. By utilization of variability in electrophoretic mobilities among charged species, spatially distinct zones of chemical reagents can be electrophoretically merged under the influence of an applied electric field. Sequential injections of different reagents into capillary are utilized to meter in reagents in the capillary. Reagent with lower electrophoretic mobility (sum of electrophoretic and electroosmotic transport velocities) is metered in first followed by reagents with higher electrophoretic mobility. Mixing occurs when the reagent with higher electrophoretic mobility overtakes the reagent with lower electrophoretic mobility.

Regneir, et al., supra, describe another concept in reaction based chemical analysis. However, this concept does not appear to be applicable to microfluidic devices. One problem is that the electrophoretic mobility of all the components in the reaction need to be known. In high throughput screening applications the electrophoretic mobility of test compounds is unknown. In the above methodology the spatial positioning of the analytes and analytical reagent zones in the capillary is determined by the sign and magnitude of the electrophoretic mobility of the various species involved so that the appropriate reagents approach and engage each other under the influence of an applied electric field. If the electrophoretic mobility of one of the analytes is not known, then determining the sequence of injections of different reagents is not possible. Another problem is that the authors mention that nonspecific binding of proteins to capillary walls is a major problem. Another problem is formation poor plugs (as identified by poor peak shapes or skewed peaks) due to unwanted protein and capillary wall interactions (adsorption-desorption), hydrophobic interactions, and ion-exchange interactions. Another problem appears to be that, when the electrophoretic mobility of two reagents vary substantially, full interpenetrating will be difficult to achieve even under high electric field strengths. For example, the ability to mix a positively charged enzyme with a negatively charged substrate is a problem that has not been addressed by the authors.

G. M. Whitesides, et al. (*J. Med. Chem.* 1993, 36:126–133; 1992, 35:2915–17;) describe a similar concept. They selected carbonic anhydrase and arylsulfonamides to determine kinetic and equilibrium binding constants. The nonspecific binding of both carbonic anhydrase and arylsulfonamides to capillary walls is limited. Whitesides, et al. (*J. Org. Chem.* 1993, 58:5508–5512) describe two types of enzyme-catalyzed reactions in electrophoresis capillaries. These reactions illustrate the interplay of the mobilities of the enzyme, substrates and products in the analysis of electropherograms during the reaction in the capillary. Whitesides points out that, to study protein ligand interactions by affinity capillary electrophoresis or enzyme catalyzed reactions in capillaries, the adsorption of protein to the surface of the capillary should be minimum.

Ramsey, et al. *Anal. Chem.* 1997, 69:3407–3412) demonstrated an enzyme (β-galactosidase) assay within a microfabricated network. The authors used electrophoretic flow to control the dilution of the reagents used in β-galactosidase assay. Even though this paper demonstrates the power of precise metering and mixing of reagents in a microfluidic device, it clearly admits that protein adsorption to channel walls will be a major problem. For example, enzyme and inhibitor dilution is performed by manually adding different concentration of enzymes and inhibitor to the reservoir. Multiple runs on the device is not practical as the background signal due to enzyme adsorption increases from run to run.

Girault, et al. (*Anal. Chem.* 1997, 69:2035–2042) describe the use of BSA to coat plasma treated microfluidic devices to reduce nonspecific binding of proteins and yet maintain electroosmotic flow. Harrison, et al. (*Clin Chem.* 1998, 44(3):591–598; *Anal. Chem.* 1997, 69:1564–1568) describe the use of bovine serum albumin (BSA) to dynamically coat microfluidic devices to reduce nonspecific binding. The apparent problems of dynamic coating with BSA appear to be that BSA does not prevent nonspecific binding completely, that the electroosmotic flow generated by BSA is pH dependent and that positively charged proteins stick to BSA coated surfaces.

Concentration of biological samples on a microliter scale and analysis by capillary electrophoresis is discussed in U.S. Pat. No. 5,766,435 by Liao, et al.

SUMMARY OF THE INVENTION

One aspect of the present invention concerns a method of controlling the direction and transport of a material by electroosmotic flow of a fluid containing the material. The method comprises providing an effective amount of at least one charged hydrophilic polymer in the fluid wherein charges on the charged hydrophilic polymer are randomly distributed.

Another aspect of the present invention is a method for transporting a liquid containing a material such as a protein in a channel of a microfluidic system by electrokinetic action, also known as electrokinesis, wherein the material comprises a plurality of differentially charged chemical species. An effective amount of at least one charged hydrophilic polymer is provided in the liquid. The charges on the charged hydrophilic polymer are randomly distributed and the charged hydrophilic polymer exhibits only transient binding to the inside wall of the channel. A voltage is applied from one point along the channel to a different point along the channel whereby the differentially charged chemical species are transported along the channel.

Another aspect of the present invention is a buffer comprising an aqueous medium of pH about 3 to about 12 and an effective amount of at least one positively or negatively charged polysaccharide.

Another aspect of the present invention is a microfluidic system comprising a microfluidic device. The device comprises at least one microfluidic network of cavity structures and channels for conducting a microfluidic process. At least one of the channels contains an electrokinesis buffer as described above.

Another aspect of the present invention is a kit comprising in packaged combination a microfluidic device and a buffer as described above.

DESCRIPTION OF THE SPECIFIC EMBODIMENTS

Figure 1:
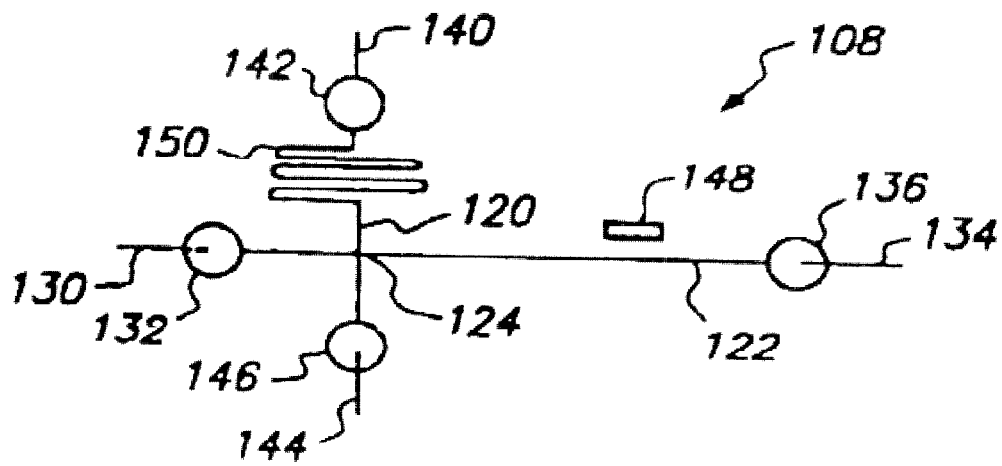
FIG. 1 is a schematic diagram of a microfluidic network.

The methods of the present invention use charged hydrophilic polymers to provide active electroosmotic flow and snarp protein bands in microfluidic devices. A charged hydrophilic polymer is present in an electrokinesis buffer to provide efficient transport of large charged molecules that have a tendency to stick to surfaces such as the inside walls of a capillary and particularly to hydrophobic surfaces. The hydrophilic polymer is employed in an electrokinesis buffer to transport and mix reagents in a microfluidics device by an electric field so that all components can be transported and mixed. The invention may be used with many surfaces including both plastic and glass surfaces, so long as the surface is charged or is modified to have charges. Thus, depending on the desired charge of the surface, polymers or surfaces having monomers or groups having positive charges, such as amine, ammonium or phosphonium may be used, or negative charges, such as glass (silanols), acrylic or methacrylic acid, etc. The surface of the channel may be modified to introduce charges, depending on the nature of the polymer and the desired charge. For example, polyacrylates and poly(methyl methacrylates) may be partially hydrolyzed to produce carboxy groups having negative charges at basic pH, or the esters may be reacted with a diamine to introduce amino groups with a positive charge at mildly acidic pH. In the present invention negatively charged, positively charged and neutral species can be transported by the EOF in a single electrokinesis buffer.

Another consideration for transport and mixing in a microfluidics device is possible adsorption of the transported species, particularly the adsorption of proteins and hydrophobic compounds. By choosing hydrophilic polymers for incorporation into the electrophoresis medium, adsorption of proteins and hydrophobic compounds are minimized. In one particular embodiment in accordance with the present invention, positively charged (cationic) or negatively charged (anionic) polysaccharides are employed to provide active electroosmotic flow for separation of proteins into sharp bands in microfluidic devices. The ionic moieties are randomly distributed on the hydrophilic polymer. Such random distribution of the charged functionalities reduces or eliminates the sticking of proteins to molecules that are highly positively charged. The use of the polymers of the present invention allows for the efficient movement of the same and oppositely charged entities, to that of the hydrophilic polymer. Furthermore, the hydrophilic polymer would appear to exhibit only transient binding to the channel of a microfluidic device.

The charged polysaccharides employed in one particular embodiment of the invention provide for low non-specific binding of the solution components to the polysaccharides and stability over a wide pH range. Protein absorption to surfaces is minimized. Substantial EOF may be generated and can be used to move neutral, anionic and cationic test compounds, including enzyme substrates and products. The hydrophilic polymers employed do not interact to any significant extent with other components in the buffer under the electroosmotic conditions, including proteins.

The present invention provides compositions, microfluidic devices and methods of analysis that do not present the drawbacks of known methods and are inexpensive, practical and easy to use providing a simple reproducible procedure.

One of the advantages of the methods and compositions of the present invention is that they provide a direct stabilization of cathodal and anodal EOF of a microfluidic device with low non-specific binding of large molecular weight proteins. Another advantage of the present invention is that positively charged proteins can be transported at neutral pH and mixed with neutral or negatively charged reagents to initiate reactions. The products of the reaction, namely, negatively charged, neutral and positively charged products, are separated in a microfluidic device without changing polarity and increasing analysis time. The methods of the present invention avoid derivatization of channel walls to form permanent bonds, which is an approach that dramatically increases the cost of a microfluidic device. Yet another advantage of the present invention is that a user can perform a number of different assays in succession on the microfluidic device without cleaning the microfluidic device. For example, an IC50 curve can be generated for an enzyme reaction in a single microfluidic device without having to worry about nonspecific binding of protein, substrate or test compound. Another advantage of the present invention is that precise fluid control can be attained. Thus, the present invention has particular application to the study of reaction systems in which reagent concentrations are dynamically changed within a single experiment.

As mentioned above, one aspect of the present invention concerns a method of controlling the direction and transport of a material of interest by electroosmotic flow of a fluid containing the material. The method comprises providing an effective amount of at least one charged hydrophilic polymer in the fluid to stabilize EOF and minimize channel wall adsorption, wherein charges on the charged hydrophilic polymer are randomly distributed.

The hydrophilic polymer employed is an assemblage of repeating or monomeric units, where the monomeric units form the backbone of the polymer. The hydrophilic polymer is compatible with water, preferably, water soluble at least to the extent that substantial EOF may be generated in an electrokinesis buffer comprising the hydrophilic polymer. Preferably, the hydrophilic polymer is water soluble at ambient conditions to the extent of at least about 1 weight percent, preferably at least about 5 weight percent. The molecular weight of the polymer should be at least 5000, preferably at least about 10,000. Usually, the molecular weight is in the range of about 10,000 to about 10 million, usually, about 100,000 to about 2 million. The predominant atom in the hydrophilic polymer is usually carbon. The polymer may contain at least 20% on an atomic weight basis of heteroatoms, e.g., oxygen (O), nitrogen (N), sulfur (S), phosphorus (P) and the like. The O, N, S, or P may be bound to carbon or one or more of each other or to hydrogen to form various functional groups, which may be a charged functionality. The functional groups include, for example, carboxyl groups (carboxylic acids), hydroxyl groups, mercapto groups, carboxamides, carbamates, carboxylic acid esters, sulfonic acids, sulfonic acid esters, phosphoric acids, phosphoric acid esters, ureas, carbamates, phosphoramides, sulfonamides, ethers, sulfides, thioethers, olefins, acetylenes, amines, ketones, aldehydes and nitrites, and alkyl, alkylidine, aryl, aralkyl, and alkyl, aryl, and aralkyl substituted with one or more of the aforementioned functional groups, and the like. The hydrophilic polymer may have on the average at least one hydroxyl group per 10 carbon atoms, generally ranging from about 1.1 to 8 carbon atoms, for sugars there will usually be about one oxy group per about 1 to 1.2 carbon atoms.

Generally, the number of charged functionaries on the hydrophilic polymer is not so great as to have the charged polymer bind more than transiently to the surface that it contacts, but great enough to provide the desired EOF. The hydrophilic polymer generally his on the average at least one charged functionality per about 100 atoms (not counting hydrogen atoms) and usually not more than one charged functionality on the average per about 12 atoms (not counting hydrogen atoms). Charged functionalities should be separated on the average by at least about 6, more usually at least about 10 atoms. Usually, there will be a low incidence of more than about 3 charged functionalities within about 18 carbon atoms. Accordingly, the charge density is usually on the average about 1 charge per about 1 repeating unit of the polymer to about 1 charge per about 60 repeating units, more usually per about 30 repeating units, of the polymer. On the average means that the number of atoms or repeating units per charge may not be the same for each set of atoms or repeating units bearing a charge but is the average number over all the sets of atoms or repeating units.

In one embodiment the hydrophilic polymer is a polyether, i.e., a polymer comprising repeating units or monomeric units connected by ether linkages. In one embodiment the polyethers are of at least about 5 kDal and may be represented by the formula:

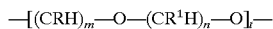

wherein R and $R^1$ are independently H, alkyl, cycloalkyl, alkenyl, cycloalkyl ether, cycloalkyl thioether, cycloalkyl-silyl ether, and the like, or may be taken together to form a ring of 5 to 7 carbon atoms, preferably, 5 to 6 carbon atoms, which ring may be substituted with one or more substituents, wherein m and n are each independently an integer of 2 to about 10, preferably, about 2 to 4, wherein m is 1 when R and $R^1$ are taken together to form a ring, wherein t is about 2 to about 50,000, preferably, about 500 to about 15,000, and wherein the polymer may terminate in H, hydroxyl, amine, ammonium, carboxylic acid and so forth.

Alkyl means a branched or unbranched saturated monovalent hydrocarbon radical containing 1 to 30 or more carbon atoms, such as methyl, ethyl, propyl, tert-butyl, n-hexyl, n-octyl and the like. Cycloalkyl means a saturated monovalent monocyclic hydrocarbon radical containing 3–8 annular carbon atoms, such as cyclopropyl, cyclobutyl, cyclopentyl, cyclohexyl, cycloheptyl and cyclooctyl. Alkenyl means a branched or unbranched unsaturated hydrocarbon radical containing at least one ethenylic bond (carbon-carbon double bond) and 2 to 10 carbon atoms.

Substituted means that a hydrogen atom of a molecule, such as a carbon atom of a ring in the above structure, has been replaced by a substituent, which is another atom that may be a single atom or part of a group of atoms forming a functionality. The substituent is an organic radical, which may have 1 to 50 atoms other than the requisite number of hydrogen atoms necessary to satisfy the valencies of the atoms in the radical. Generally, the predominant atom is carbon but may also include oxygen, nitrogen, sulfur, phosphorus, wherein the O, N, S, or P, if present, are bound to carbon or one or more of each other or to hydrogen to form various functional groups, such as, for example, carboxyl groups, hydroxyl groups, mercapto groups (thiols), phosphates, sulfates, phosphonium ions, amino and ammonium ions. Preferably, the substituent of the ring is a hydroxyl or a hydroxyl substituted with sulfate, phosphate, carboxyl, polyiminoalkylene, hydroxyl substituted polyiminoalkylene, substituted polyphosphonium alkylene, substituted polyphosphorus alkylene, and the like, where the iminoalkylenes are of from about 4 to 30 carbon atoms and have one amino group per 2 to 12 carbon atoms and from about 2 to 6 amino groups, the alkylene groups being of from about 2 to 12 carbon atoms.

Polyethers include, for example, polysaccharides, polyalkylene glycol, where the alkylenes are of from 2 to 6 carbon atoms, and the like. Preferred hydrophilic polymers in accordance with the present invention are polysaccharides. For polysaccharides the monomeric units may be one or a mixture of saccharides such as, for example, glucose, mannose, galactose, arabinose, altrose, gulose, iodose, talose and the like. The ratio of different saccharides in the hydrophilic polymer may be, e.g., about 1:1 to about 1:100. When the monomeric unit is glucose, the polymer may be, for example, a dextran and so forth. When the monomeric unit is alternately mannose and galactose, the polymer may be, for example, a guaran and so forth. Other polysaccharides include pullulans, konjacs, locust bean gum, agars, alginates, chitins, β-glucans, heparins, pectins, starches, tragacanthis gums and xanthum. In one embodiment the polysaccharide cancomprise polyiminoalkylene groups linked to a hydroxyl of the saccharide monomeric unit. The number of amino groups within, the polyiminoalkylene groups may be on the average about one per about 3 carbon atoms to about one per about 30 carbon atoms.

Examples of charged hydrophilic polymers of the present invention, by way of illustration and not limitation, are set forth below wherein m is the number of saccharide monomer units and n is the number of saccharide monomer on the average per substituent carrying a charge-imparting moiety. On the average means that the number of saccharide monomer units per substituent carrying charge-imparting moieties may not be the same for each set of saccharide monomer units bearing a substituent but is the average number over all the sets of saccharide monomers. Compound E where n=3 is available from Sigma Chemical Company.

Substituted AminoDextrans

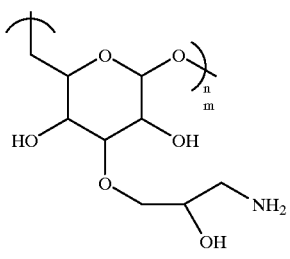

A m =~ 2810 n = 20   1
  = 15   2
  = 10   3
   = 6   4

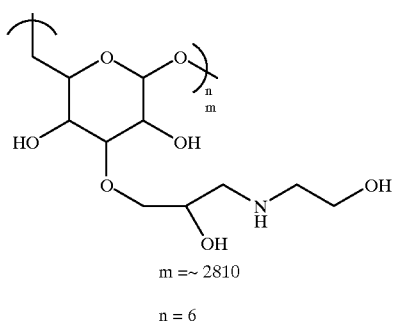

m =~ 2810 n = 6

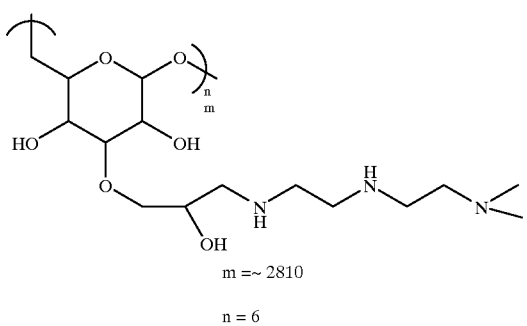

m =~ 2810 n = 6

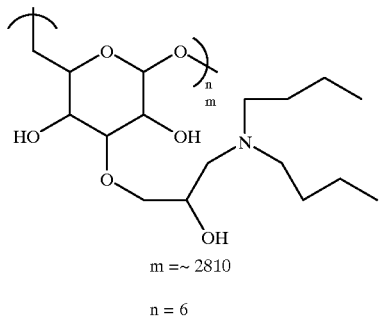

m =~ 2810 n = 6

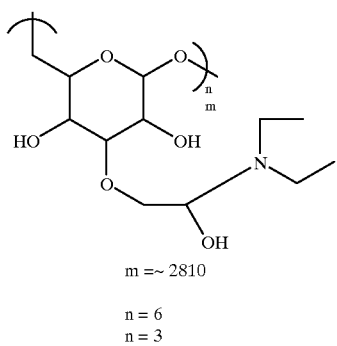

m =~ 2810 n = 6
n = 3

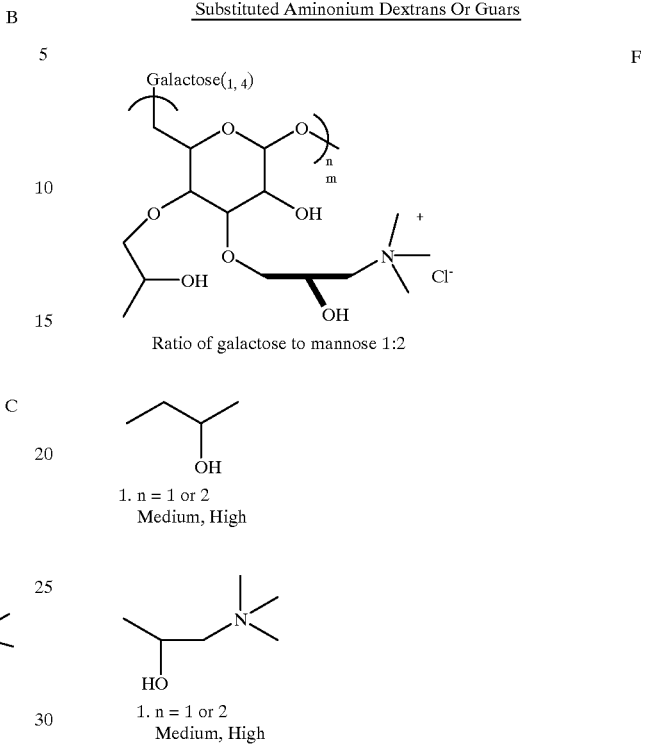

Ratio of galactose to mannose 1:2

1. n = 1 or 2
   Medium, High 1. n = 1 or 2
   Medium, High

As mentioned above, in accordance with the present invention the hydrophilic polymer comprises one or more charges. The charges may be positive or negative, and will generally all be the same charge. The charges are usually part of a substituent on the hydrophilic polymer as discussed above. In one embodiment the charge-imparting moiety may be, for example, an ammonium ion, phosphonium ion and the like. In another embodiment the charge-imparting moiety may be, for example, a carboxyl group, a sulfate group, a phosphate group and the like.

In preparing the hydrophilic polymers of the present invention, one or more of the monomeric units of the polymer may be modified to contain a functionality for linking to a charge-imparting group. Such functionalities may be groups such as hydroxymethyl-, hydroxyethyl-, hydroxyl propyl-, hydroxybenzyl-, hydroxyethylamino-, hydroxypropylamino- and the like. Functionalities for linking to charge-imparting groups may be introduced by oxidation reactions, reduction reactions, elimination reactions, condensation reactions, alkylation reactions, and so forth. The type of reaction involved in the introduction of the appropriate functionality depends on the type of reactants used and can thus be selected according to the desired functionality to be introduced. A summary of such reactions may be found in "Modern Synthetic Reactions," Second Edition, The Benjamin/Cummings Publishing Company, Menlo Park, Calif., H. O. House, Organic Chemistry by J. March.

The charge-imparting groups may be bound directly to the functionality or may be bound through the intermediacy of a linking group or spacer group as discussed above with respect to the substituent. The linking group may vary from a bond to a chain of from 1 to about 50 atoms, usually from about 2 to about 20 atoms, each independently selected from the group normally consisting of carbon, oxygen, sulfur, nitrogen, halogen and phosphorous. The number of heteroatoms in the linking groups will normally range from about 0 to 10, usually from about 1 to 5. The atoms in the chain may be substituted with atoms other than hydrogen in a manner similar to that described above for the substituent and consistent with the function of the linking group, namely, linking the charge-imparting group to the polymer backbone. As a general rule, the length of a particular linking group can be selected arbitrarily to provide for convenience of synthesis and the incorporation of any desired charge-imparting group. The linking groups may be aliphatic or aromatic. For the most part the linking group will be from about 2 to 10 total atoms other than hydrogen, having from about 0 to 3 heteroatoms, which are chalcogen, oxygen or sulfur, nitrogen, where the chalcogen will be present as ether or carbonyl and the nitrogen present as amino, imino or ammonium.

In one approach, for example, positively charged polymers may be synthesized by attaching groups with amine functionalities to the polymer backbone, usually by means of a functionality on the polymer backbone. Such groups may be amino-, methylamino-, ethanolamino-, dimethylamino-, diedmanolamino-, diethylenetriamino-, diethylaminoethyl-trimethylammonium- and other substituted ammonium-groups. For phosphonium ions such groups include, for example, methyl phosphine, dimethyl phosphine, diethanol phosphine, trimethyl phosphonium and the like. By employing polymers having a plurality of reactive functional groups, particularly, each monomer having at least one reactive functional group, and combining the polymer with a reactive species which provides a positive charge, where the ratio of reactive functionalities on the polymer to the molecules of reactive species is not greater than one, usually not greater than 0.5, depending on the efficiency of reaction, the rate of reaction and the ease of monitoring the extent of reaction. Where one monitors the reaction, the ratio may be higher than one by interrupting the reaction before completion, but the effective ratio, that amount of the reactive species that has reacted, will be less than one.

The random distribution of the charge-imparting moieties on the polymer backbone is obtained during the synthesis of the charged hydrophilic polymer. One way of achieving the random distribution involves varying the concentration of the reactive species relative to that of the polymer. For example, for introducing ammonium groups, a polysaccharide may be reacted with different concentrations (or equivalents) of ammonium epoxide to obtain a distribution of one ammonium group for 2 repeating units to one ammonium group for 20 repeating units.

Examples, by way of illustration and not limitation, of introducing charge-imparting groups, are discussed for each of the above groups. Polymers containing ammonium groups may be synthesized, for example, by reacting the polymer with an appropriately substituted epoxide or by reacting a functionalized polymer, e.g., a haloalkyl polymer, with a suitable amine. An example of the former approach may be applied to the synthesis of a polysaccharide such as those mentioned above. The alkylene-substituted epoxide is prepared to contain the desired number of amine functionalities in the alkylene substituent. The substituted epoxide is then reacted with the polysaccharide under conditions for reaction of a hydroxyl group of the polysaccharide with the epoxide. Such conditions are well-known to those skilled in the art. In an example of the latter approach as applied to polysaccharides, the polymer is prepared with the desired number of haloalkyl chains linked to hydroxyl groups of the polymer. The substituted product is then reacted with the appropriate amine under conditions for reaction of the amine with the halo groups on the alkylene chains on the polysaccharide. Such conditions are also well-known to those skilled in the art. Other methods may employ glycidyl halides.

Similar approaches may be used in the preparation of hydrophilic polymers substituted with other types of charge-imparting moieties. Polymers containing phosphonium groups may be synthesized, for example, by reacting the polymer with an appropriately substituted epoxtide or by reacting the phosphine with a halogen or tosylate substituted polymer. In another approach aldehyde or ketone substituted polymers can be reacted with appropriate phosphines.

Negative charge-imparting moieties of negatively charged hydrophilic polymers may be, for example, carboxyl groups, sulfate groups, phosphate groups and so forth. Negatively charged polymers may be functionalized to contain carboxyl functionalities such as, for example, compounds A to F above. Polymers containing carboxyl functionalities may be synthesized, for example, by reacting the polymer with halogen substituted carboxylic acids such as, e.g., bromoacetic acid, or by reacting the polymer with epoxy acids or olefin-containing carboxylic acids such as, e.g., acrylic acid. Polymers containing sulfate functionalities may be synthesized by reacting the polymer with a sulfuryl halide or by a method similar to one discussed above for the synthesis of carboxylic acids. Polymers containing phosphate functionalities may be synthesized by reacting the polymers with, e.g., phosphoryl chlorides as well as by a method similar to those discussed above for the introduction of other functionalities. Other methods of synthesis will be evident to those skilled in the art.

As mentioned above, the charges on the charged hydrophilic polymer are randomly distributed. The charges on the polymer backbone are randomly distributed when there is no particular distribution to the presence of the charge-imparting moieties on the polymer backbone, that is, the spacing between charged functionalities is random, with no one spacing being greater than about 35%, except where there is a substituent which includes a plurality of charged functionalities, which plurality should not exceed three, preferably not exceed two. The random distribution of the charge-imparting moieties appears to minimize binding of the polymer to the channel wall and protein to the channel wall. The polymers are typically synthesized, as described above, to contain the desired charge density (number of charge-imparting moieties/monomer unit or repeating unit) in order to obtain the desired EOF. The desired charge density and surface properties may be determined empirically and in some instances achieved by using mixtures of these polymers.

The random distribution of charge-imparting moieties, or charge density, in accordance with the present invention allows one to perform separations of material such as differentially charged chemical species and the like. Unlike other systems known in the art, the present invention permits movement of materials with different charges and/or no charges and/or hydrophobic material in the same electrokinesis buffer.

The charged hydrophilic polymer in accordance with the present invention is employed dynamically in an electrokinesis buffer. This buffer is generally an electrophoresis medium or an electroflow medium or an electrically conductive medium. The electrokinesis buffer is a aqueous medium generally utilized in carrying out electrokinetic processes. The medium chosen is one that is suitable to a particular application of interest. The medium should not interfere to any substantial degree with the electric fields used when utilizing microfluidic devices.

The electrokinesis buffer may be a conventional buffer such as, for example, the Good's buffers (HEPES, MOPS, MES, Tricine, etc.), and other organic buffers (Tris, acetate, citrate, and formate), including standard inorganic compounds (phosphate, borate, etc.). Exemplary buffer systems include: (i) 100 mM sodium phosphate, pH 7.2; (ii) 20 mM tris-base, 20 mM boric acid, 2 mM ETDA, pH 8.3; or (iii) 25 mM Hepes, pH 7.5. Buffer additives include methanol, dimethylsulfoxide, dimethylformamide, $CH_3CN$, metal ions, urea, surfactants, and intercalating dyes and other labeling reagents. Inert polymers can be added to the separation buffer to stabilize the separation matrix against factors such as convection mixing. The buffer may also contain any other material that does not interfere with the functional behavior of the buffer, the charged hydrophilic polymer, the microfluidic processing to be conducted, and so forth.

The charged hydrophilic polymer is present in the electrokinesis buffer in an effective amount, which is the amount of the charged hydrophilic polymer in an electrokinesis buffer that results in the desired EOF. The amount that may be effective to achieve this result is dependent on the nature of the charged hydrophilic polymer, the nature of the surface such as an interior wall of a channel, ionic strength, nature of reaction or assay, and the like. The effective amount is usually determined empirically using the charged hydrophilic polymer in an electrokinesis buffer in a particular device. In general, an effective amount of the charged hydrophilic polymer is about 0.0015% to about 5% by weight, usually, about 0.02% to about 0.5% by weight, of the electrokinesis buffer. As mentioned above, binding of the charged hydrophilic polymers to a surface may be further controlled by the use of only relatively low concentrations of the polymer in the electrokinesis buffer.

The pH of the electrokinesis buffer is usually about 3 to about 12, more usually, about 4 to about 10. The pH is generally chosen to optimize the EOF, which usually involves selecting the pH that results in the ionic character of the charge-imparting groups. The desired EOF is that which permits the performance of the microfluidic process conducted. In general, the EOF is about $40 \times 10^{-5}$ to about $2 \times 10^{-5}$ $cm^2$ per volts per second, usually, about $20 \times 10^{-5}$ to about $5 \times 10^{-5}$ $cm^2$ per volts per second. With negative values for EOF, the ligand flows towards the anode.

As mentioned above, the present method involves controlling the direction and transport of a material by electroosmotic flow of a liquid containing the material. The material may be a ligand or receptor, which is synthetic or natural, antigenic or haptenic, a single compound or plurality of compounds. The material may be a test compound from a combinatorial library, a pharmacophore from an existing library, and the like. The low molecular weight ligands have a molecular weight from about 100 to 5,000, more usually from 125 to 2,000, and include drugs, potential drug candidates, metabolites, pesticides, pollutants, and the like. Higher molecular weight ligands generally have a molecular weight of at least about 5,000, more usually at least about 10,000, and include, for example poly(amino acids) such as proteins, polynucleotides, immunoglobulins, enzymes, receptors, and so forth. Receptors include such materials as naturally occurring receptors, synthetic receptors, polynucleotides, membrane bound receptors and so forth. Polynucleotides include m-RNA, r-RNA, t-RNA, DNA, cDNA, DNA-RNA duplexes, etc. Illustrative membrane bound receptors include G-protein receptors (e.g., muscarinic, adrenergic, prostaglandin and dopamine such as the D2 receptor), tyrosine kinase (insulin-like IGF, epidermal EGF, nerve NGF, fibroblast FGF growth factors), ion channels, T-cell receptors, the interleukins, and other naturally occurring receptors, e.g., thyroxine binding globulin, antibodies, enzymes, Fab fragments, lectins, nucleic acids, protein A, complement component C1q, and the like. The material of interest also includes receptors that are polynucleotide binding agents, such as, for example, restriction enzymes, activators, repressors, nucleases, polymerases, histones, repair enzymes, chemotherapeutic agents, and the like. Also included are combinations of receptors such as components of bacteria, viruses, fungi, protozoan, chromosomes, genes, mitochondria, nuclei, cell membranes and the like.

A differentially charged chemical species is one of a group of materials of interest. The differentially charged chemical species may comprise materials that are neutral or are comprised of one or more positive or negative charges. The materials may differ by having different numbers of one charge such as different numbers of positive charges or negative charges. Examples of differentially charged chemical species, by way of illustration and not limitation, include proteins, polynucleotides, test compounds from a combinatorial library, cofactors, pharmacophores, and the like. The charge of the differentially charged chemical species may depend on the pH of the medium in which they are found. For example, proteins have different charge distribution based on pH and isoelectric point. It is a significant advantage of the present invention that the differentially charged chemical species subjected to the present methods may include neutral as well as positively and negatively charged materials to be separated in the same electrokinesis buffer.

The electrokinesis buffer of the present invention has broad application in the field of electrophoresis and electroosmotic flow, as related to microfluidic processing. Electrophoresis generally involves separation of components in a liquid by electroflow. Various forms of electrophoresis include, by way of example and not limitation, free zone electrophoresis, gel electrophoresis, isotachophoresis, high performance CE, capillary zone electrophoresis, isoelectric focusing, micellar electrokinetic capillary chromatography, and the like. An electrophoresis column in the context of the present invention is a channel for carrying out electrophoresis.

Electroflow generally involves the manipulation of entities or species such as molecules, particles, cells and the like through a medium under the influence of an applied electric field by use of electrodes and the like to induce movement such as electrokinetic flow including, electroosmotic flow, electrophoretic flow, dielectrophoretic flow, and so forth. Depending on the nature of the entities, e.g., whether or not they carry an electrical charge, as well as the surface chemistry of the chamber in which the electroflow is conducted, the entities may be moved through the medium under the direct influence of the applied electric field or as a result of bulk fluid flow through the pathway resulting from the application of the electric field, e.g., electroosmotic flow. It is within the purview of the present invention that electroflow can be carried out in conjunction with movement of material by gravity or by application of a magnetic field, centrifugal force, thermal gradients, pneumatic means including negative (vacuum) and positive (pumping) pressure, and the like.

Often, a microfluidic network is employed, which is a system of interconnected cavity structures and capillary-size channels configured with a plurality of branches through which fluids may be manipulated and processed. A cavity structure is an unfilled space, preferably, a hollowed out space in an object, such as, e.g., a planar substrate, a plate, or the like such as, for example, a well, a reservoir, an incubation chamber, a separation chamber, an enrichment chamber, a detection chamber, and the like. The cavity structures are usually present at one, or both of the termini, i.e., either end, of a channel. The cavity structures may serve a variety of purposes, such as, for example, means for introducing a buffer solution, elution solvent, reagent rinse and wash solutions, and so forth into a main channel or one or more interconnected auxiliary channels, receiving waste fluid from the main channel, and the like. Channels provide a conduit or means of communication, usually fluid communication, more particularly, liquid communication, between elements of the present apparatus. The elements in communication are, e.g., cavity structures, and the like. Channels include capillaries, grooves, trenches, microflumes, and so forth. The channels may be straight, curved, serpentine, labyrinth-like or other convenient configuration within the planar substrate. The cross-sectional shape of the channel may be circular, ellipsoid, square, rectangular, triangular and the like so that it forms a microchannel within the substrate in which it is present.

The channels and the like are usually of capillary dimension, i.e., having a cross-sectional area that provides for capillary flow through a channel. At least one of the cross-sectional dimensions, e.g., width, height, diameter, is at least about 1 $\mu$m, usually at least 10 $\mu$m, and is usually no more than 500 $\mu$m, preferably no more than 200 $\mu$m. Channels of capillary dimension typically have an inside bore diameter (ID) of from about 1 to 200 microns, more typically from about 25 to 100 microns, with cross-sections of greater than 100 microns, generally in the range of about 250 to 5000 microns.

Sample processing is usually carried out on a microfluidic scale. The processing involves fluid handling, transport and manipulation within chambers and channels of capillary dimension. Valveless sample injection is achieved by moving fluid from the reagent reservoirs into cross-channel injection zones, where plugs of buffer or test compounds are precisely metered and dispensed into a desired flowpath. The rate and timing of movement of the fluids in the various microchannels can be controlled by electrokinetic, magnetic, pneumatic, and/or thermal-gradient driven transport, among others. These sample manipulation methods enable the profile and volume of the fluid plug to be controlled over a range of sizes with high reproducibility. In addition, microfluidic processing may include sample preparation and isolation where enrichment microchannels containing separation media are employed for target capture and purification. Microfluidic processing may also include reagent mixing, reaction/incubation, separations and sample detection and analyses. Reactions may include catalytic and affinity reactions. Although enzymes are the typical biocatalyst employed for bioanalytical applications, catalytic antibodies and catalytic RNA are also to be included, among others. Affinity-based reactions may include, but are not limited to, receptor-mediated ligand binding, DNA or RNA hybridization, and immuno-reactions. The later is not limited to antibody-antigen interactions and can include antibody-hapten, antibody-nucleic acid binding, antibody-antibody interactions, and antibody-receptor binding.

A sample may be processed by one or more of any number of procedures such as, for example, separating or classifying compounds, replicating or amplifying components, degrading components, polymerizing components, and other similar modifications, and so forth. Examples of such procedures include subjecting a sample to separation procedures for sample enrichment, isolation or purification, analyzing such sample such as, e.g., assay, detection and the like, carrying out a chemical synthesis with such sample, such as those involved with combinatorial chemistry methods for small and large molecule synthesis, screening for therapeutic drugs, receptor-ligand binding analysis, screening for agonist/antagonist behavior of compounds, DNA and protein sequencing, genotyping, oligosaccharide profiling, and so forth. For example, polynucleotides may be synthesized or sequenced. Different nucleotides can be reacted to form DNA and different amino acids can be reacted to form proteins.

In addition to the separation, synthesis and sequencing methods described above, the present invention is useful for a variety of additional purposes. For example, it is possible to utilize specific embodiments of the invention in order to separate impurities from large mixtures of compounds and thus carry out a purification processing which is substantially more refined than vacuum fractionation processing. A mixture of components can be separated into a variety of pure groups and moved along parallel tracks. Upon resolving the mixtures, the desired components can be guided by the electrical fields to appropriate locations within one or more channels. Alternatively, selected components may be guided to channels filled with members of binding pairs, such as antigen-antibody pairs, reactive with given substances of interest. These materials of interest may be moving in the medium or be moved into contact with complementary components having a label, other member of a signal producing system, or other type of chemical for various transformations that are either physical or chemical in nature. Furthermore, bacterial or mammalian cells, or viruses may be sorted by complicated microfluidic networks in connection with a plurality of electrodes capable of generating electrical potentials of a variety of different strengths in order to move the cells, organelles, liposomes, and the like, or viruses, through the fields based on the size, charge or shape of the particular material being moved. Separated cells or viruses may be analyzed or modified subsequently, for example, by disruption to analyze or otherwise characterize its internal components.

The processing is generally carried out on a microfluidic scale with channel dimensions similar to those used typically in capillary electrophoresis. However, there may be regions with larger than capillary-scale dimensions for purposes of increasing surface area reaction volume, accommodating highly dilute sample or interfacing with existing equipment. The miniaturized system of enrichment trenches, reaction chambers and detection zones enable multiple laboratory processes to be integrated "on-board" a planar substrate, including sample preparation, incubation, electrophoretic separations, and analyses.

The sample is usually a medium containing one or more materials of interest, such as differentially charged chemical species. Typical sources for mammalian biological samples include body fluids such as, for example, whole blood, blood fractions such as serum and plasma, synovial fluid, cerebrospinal fluid, amniotic fluid, semen, cervical mucus, sputum, saliva, gingival fluid, urine, and the like. Other sources include culture samples, bioprocessing fluids, food and beverage water, air and soil samples, and so forth. In addition, sample includes combinatorial chemistry generated libraries of compounds, usually small molecules, oligonucleotides and peptides. Other sources of samples are aqueous or water soluble solutions of natural or synthetic compounds, particularly, compounds that are potential therapeutic drugs where it is desired to determine if the compound binds to a specific receptor.

The amount of the sample depends on the nature of the sample and the nature of the processing to be conducted. For fluid samples such as whole blood, saliva, urine and the like the amount of the sample is usually about 1 to about 1000 nanoliters, more usually, about 10 to about 100 nanoliters. For samples containing other materials of interest the amount is usually about 10 to about 10,000 nanoliters, more usually, about 100 to about 1000 nanoliters. The sample can be pretreated and can be prepared in any convenient medium, which does not interfere with a microfluidic process in accordance with the present invention.

In an assay and in screening methods it is often desirable to use one or more labels or reporter molecules, which include a chemical entity capable of being detected by a suitable detection means, including, but not limited to, spectrophotometric, chemiluminescent, electrochemical or radiochemical means. The reporter molecule can be conjugated to another molecule such as a specific binding pair (sbp) member, e.g., a ligand or an antibody, by procedures well known in the art. Typically, the reporter molecule contains a functional group suitable for attachment to the sbp member. The functional groups suitable for attaching the reporter group are usually activated esters or alkylating agents. Details of techniques for attaching reporter groups are well known in the art. See, for example, Matthews, et al., *Anal. Biochem.* (1985) 151:205–209 and Engelhardt, et al., European Patent Application No. 0302175.

Reporter molecules are members of a signal producing system capable of being detected directly or through a specific binding reaction to produce a detectable signal. The reporter molecule can be isotopic or nonisotopic, usually nonisotopic, and can be a catalyst, dye, fluorescent molecule, chemiluminescent molecule, coenzyme, enzyme, substrate, radioactive group, certain particles such as carbon and the like. Thus, with the above labels the signal is preferably detected and/or measured by detecting enzyme activity, luminescence, or light emissions depending on the nature of the label. The labels and other reagents of the signal producing system must be stable at the temperatures used in the electroseparation method and any subsequent assay.

Some labels can directly produce a signal, and therefore, additional components are not required to produce a signal. Numerous organic molecules, for example fluorescers, are able to absorb ultraviolet and visible light, where the light absorption excites these molecules to an excited energy state. This absorbed energy is then dissipated by emission of light at a second wavelength. Other labels that directly produce a signal include radioactive isotopes and dyes.

Alternately, the label may need other components to produce a signal. In this situation the signal producing system would then include all the components required to produce a measurable signal. These components may include substrates, electron transfer agents, coenzymes, enhancers, additional enzymes, substances that react with enzymic products, catalysts, activators, cofactors, inhibitors, scavengers, metal ions, and a specific binding substance required for binding of signal generating substances.

As mentioned above, the microfluidic processing includes assays. Generally, an assay is a method for determining a substance capable of binding to a specific binding pair member, for example, for determining an analyte or detecting the degree of binding of a compound to a receptor. The determination may be qualitative or quantitative. Such assays depend on specific binding of a ligand to its receptor and include receptor binding assays, immunoassays, ligand/binding assays, polynucleotide assays, particularly polynucleotide hybridization assays, and cell surface binding assays. The assays may be utilized for drug discovery and screening, studies of receptors, detection of drugs and other substances, DNA detection, DNA sequencing, genetic analysis, monitoring of gene expression, and so forth. One particular assay is the immunoassay, which is a specific binding assay in which the reagents include an antibody.

Receptor-ligand binding competitive binding assays are a useful preliminary means for screening a large number of compounds for their therapeutic potential. Improved high throughput bioanalytical techniques are needed for characterizing the functional properties of receptor-mediated signaling and other cell transduction mechanisms. The receptor binding assays routinely arise in the fields of pharmacology, neurobiology, cardiology, immunology, microbiology and oncology, among others.

The assays may be heterogeneous or homogeneous. A heterogeneous assay is an assay wherein free, labeled species is separated from a labeled species that is bound to another species such as an sbp member. The separation may be carried out by physical separation, e.g., by transferring one of the species to another reaction vessel, filtration, centrifugation, chromatography, solid phase capture, magnetic separation, and so forth and may include one or more washing steps. The separation may be nonphysical in that no transfer of one or both of the species is conducted, but the species are separated from one another in situ. Regardless of the means of separation, the signal from the label may be measured from one or both of the separated species.

A homogeneous assay is an assay wherein free, labeled species is not separated from a labeled species that is bound to another species such as an sbp member. The signal from the label is significantly different between the free, labeled species and that which is bound and, thus, can be measured without separation.

The microfluidic processing carried out using the electrokinesis buffer of the present invention is conducted in a microfluidic network of a microfluidic device. As explained above, the microfluidic network has interconnected cavity structures and channels, the latter forming one or more flowpaths resulting in an interconnected system. In general, there is a main flowpath and one or more secondary flowpaths. A desired microfluidic process may be carried out in the main flowpath or in one of the secondary flowpaths. The additional flowpaths may be employed for a variety of purposes such as, for example, enrichment of a sample, isolation, purification, dilution, mixing, metering, and the like. A variety of configurations are possible, such as a branched configuration in which a plurality of flowpaths is in fluid communication with the main flowpath. See, for example, U.S. Pat. No. 5,126,022.

The main flowpath has associated with it at least one pair of electrodes for applying an electric field to the electrokinesis buffer present in the flowpath. Where a single pair of electrodes is employed, typically one member of the pair is present at each end of the pathway. Where convenient, a plurality of electrodes may be associated with the flowpath, as described in U.S. Pat. No. 5,126,022, the relevant disclosure of which is herein incorporated by reference, where the plurality of electrodes can provide for precise movement of entities along the flowpath. The electrodes employed in the subject invention may be any convenient type capable of applying an appropriate electric field to the medium present in the flowpath with which they are associated.

The surface that contacts the electrokinesis buffer, such as, e.g., inner surfaces of channels within a microfluidic device, may be activated with base before use with the electrokinesis buffer of the invention. In the presence of a basic medium, plastic surfaces generate carboxyl groups on the surface and glass and fused silica surfaces generate silanol groups on the surface. Both carboxyl groups and silanol groups are negatively charged and this negative charge aids in ionic interaction between these groups and the positively charged hydrophilic polymers of the invention. Such ionic interaction contributes to the superior surface coverage of the hydrophilic polymers, which bind transiently to, and prevent adsorption of proteins and hydrophobic compounds to, the channel surfaces. Basic media that may be employed to achieve such activation include, for example, aqueous sodium hydroxide, potassium hydroxide, and the like. The concentration of the basic medium should be sufficient to achieve the level of activation or hydrolysis desired. Usually, the level of hydrolysis will provide an EOF under the conditions described in the Experimental section in the range of about −3 to −50. In this regard and from another viewpoint, the level of hydrolysis should be sufficient to achieve the desired EOF.

The methods for hydrolysis are well within the skill of the artisan. For example, with inner walls that are comprised of acrylate, aqueous base, such as aqueous sodium hydroxide, may be employed at a concentration of about 0.5 to about 2M, preferably, about 1 to 1.5 M, usually at ambient conditions. The time of treatment is generally that necessary to achieve the desired level of hydrolysis. For example, treatment may be carried out at ambient temperature for about 1 minute to about 2 hours, usually, about 10 to about 60 minutes. Following treatment the inner walls may be washed to remove excess treatment solution. Desirably, the inner walls may also be rinsed with electrokinesis buffer. In some instances and depending on the nature of the surface an aqueous acid may be used to activate the surface. The nature and concentration of the acid is based on considerations similar to that described above.

An example of a general configuration of a microfluidic network is shown in FIG. 1. A microfluidic plate is comprised of a plurality of microfluidic networks 108. Each network comprises a main flowpath 120 and secondary flowpath 122, which intersect at 124. Electrode 130 is connected to reservoir 132 and eletrode 134 is connected to reservoir 136. An electric potential can be applied to flowpath 122 by means of electrodes 130 and 134. Electrode 140 is connected to sample introduction port and reservoir 142 and electrode 144 is connected to reservoir 146. An electric potential can be applied to main flowpath 120 by means of electrodes 140 and 144. The main flowpath 120 has optional portion 150 that is tortuous to provide an appropriate path length and residence time to achieve mixing by diffusion, incubation, and so forth.

Secondary flowpath 122 has detection zone 148 where the result of a microfluidic process may be detected. For example, if the microfluidic process is an assay for an analyte, the detection zone permits the detection of a signal produced during the assay. Alternatively, if the microfluidic process is a chemical synthesis, the detection zone may be used to detect the presence of the synthesized compound. Several detection zones may be employed depending on the nature of the microfluidic process. There may be any number of detection zones associated with a single channel or with multiple channels. Suitable detectors for use in the detection zones include, by way of example, photomultiplier tubes, photodiodes, photodiode arrays, avalanche photodiodes, linear and array charge coupled device (CCD) chips, CCD camera modules, spectrophotometers, spectrofluorometers, and the like. Excitation sources include, for example, filtered lamps, LED's, laser diodes, gas, liquid and solid state lasers, and so forth. The detection may be laser scanned excitation, CCD camera detection, coaxial fiber optics, confocal back or forward fluorescence detection in single or array configurations, and the like.

Detection may be by any of the known methods associated with the analysis of capillary electrophoresis columns including the methods shown in U.S. Pat. No. 5,560,811 (column 11, lines 19–30), U.S. Pat. Nos. 4,675,300 and 5,324,401, the relevant disclosures of which are incorporated herein by reference. An example of an optical system for reading the channels in the detection zones comprises a power supply, which energizes a photomultiplier tube. A power supply energizes a 75 watt Xenon lamp. Light from the lamp is condensed by focusing lens, which passes light to an excitation filter. A dichroic mirror directs excitation light to a microscope. The apparatus is mounted on a so that light passes over the channels. Fluorescent emission light is collected by the microscope, passed through a dichroic mirror, emission filter, or spatial filter before reaching the photomultiplier (PMT). The output signal of PMT is fed to an analog-to-digital converter, which in turn is connected to computer.

Alternatively, a static detection system in which a stationary detection point some distance from the injection end of the capillary is monitored as bands to be analyzed traverse the length of the capillary and pass by the detection zone could be used. This type of detection could be implemented using optical fibers and lenses to deliver the excitation radiation to the capillary and to collect the fluorescent emission radiation from the detection zone in the capillary. Appropriate multiplexing and demultiplexing protocols might be used to sequentially irradiate and monitor a large array of capillaries using a single source and a single or a small number of photodetectors. Using this approach, each capillary in an array is sequentially polled to detect any analyte band in the detection zone of that capillary.

The detectors may be part of an instrument into which the microfluidic device is inserted. The instrument may be the same instrument that comprises the electrode leads and other components necessary for utilizing the microfluidic device. However, separate instruments may be used for housing a sample container plate, incubation of sample and reagents, detection of a result, electrical field application, and other operations such as temperature and humidity control, and so forth. Humidity control may be achieved in a number of ways such as, for example, the use of humidistats, water vapor sources confined in the device in fluid communication with other areas thereof, and so forth. Other methods of humidity control will be evident to those skilled in the art.

Figure 4:
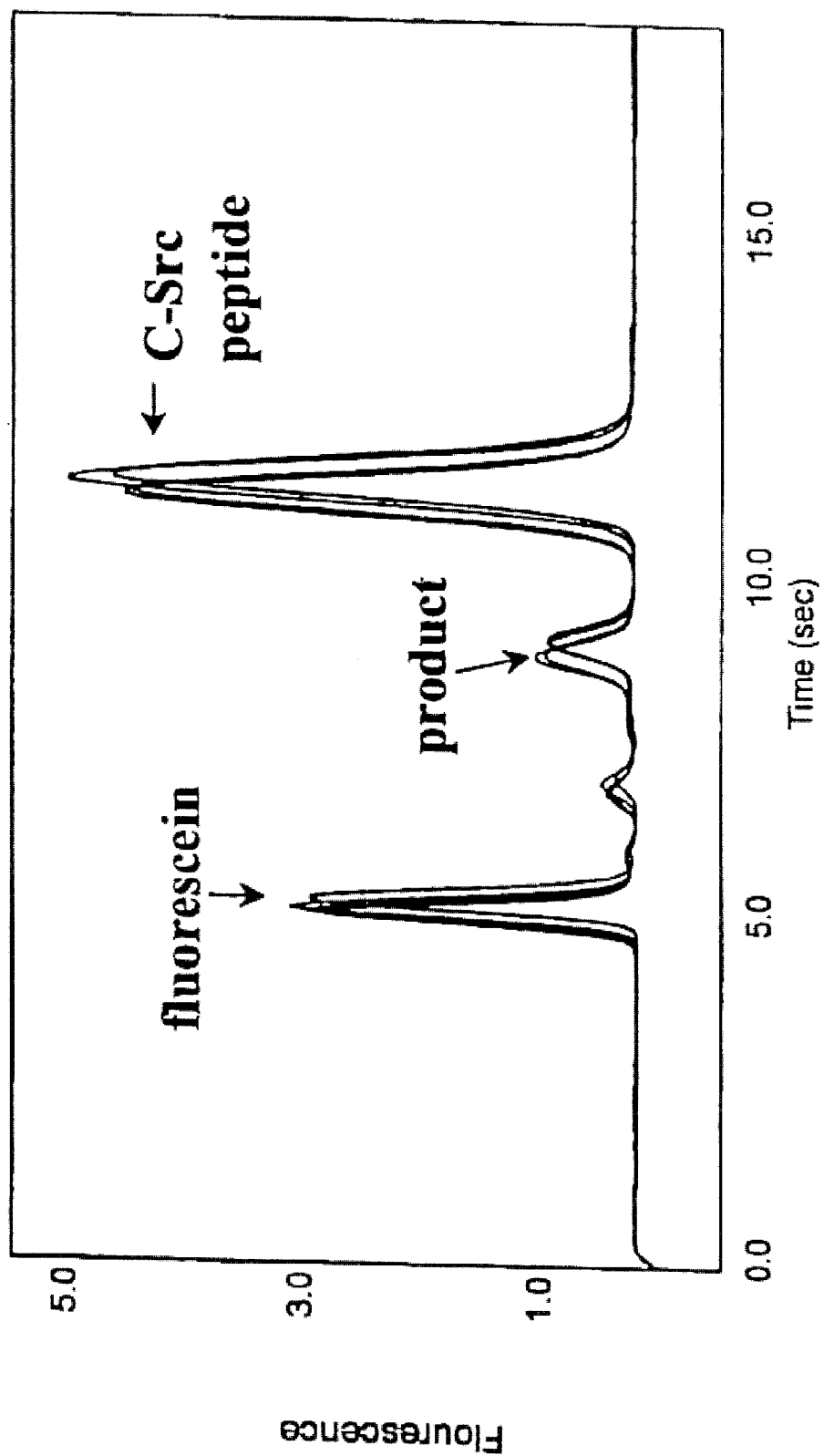
FIG. 4 is a graph depicting results of experiments carried out in accordance with the present invention.

The use of a microfluidic network is next discussed with reference to FIG. 4. The channels of the microfluidic device may be pre-filled with electrokinesis buffer of the invention, usually by pumping a desired amount of the buffer into and through at least the channels where microfluidic processing will take place. Then, sample in the electrokinesis buffer is introduced into sample introduction port and reservoir 142 together with appropriate reagents for carrying out a microfluidic process. An electric potential is applied across electrodes 140 and 144 causing medium containing the sample and other reagents to move through flowpath 120 and, in particular, portion 150 of 120. Mixing of sample and reagents, as well as incubation, take place in portion 150. When the portion of the medium containing, the sample and reagents reaches intersection 124, the electric potential applied between electrodes 140 and 144 is discontinued and an electric potential is applied between electrodes 130 and 134. The point at which the sample and other reagents reach intersection 124 may be determined by detecting the presence of the sample or one of the reagents directly or by empirically determining the time at which the sample and reagents should reach the intersection 124, based on the particular nature of the sample, the medium employed, the strength of the electric potential, the nature of the EOF and so forth. Application of the electrical potential to electrodes 130 and 134 causes a plug of medium of precise amount (determined by the dimensions of the channel) to move along secondary flowpath 122 towards reservoir 136 and through detection zone 148 where detection is conducted. This is the basic manner in which an exemplary microfluidic network operates.

Of course, as will be appreciated by one of ordinary skill in the art, the precise manner of operation of microfluidic networks in an apparatus is dependent on the construction of the apparatus. Considerations include, for example, whether reagents are present on board the apparatus or added from a source outside the apparatus. Other considerations include manipulation of beads or magnetic beads in the channels, filling of channels with buffer, manipulation of discrete drops within otherwise unfilled channels, method of fluid movement (electroosmotic, electrokinetic, surface tension, centrifugal, pneumatic), mixing two or more reagents, incubation, and so forth.

Those skilled in the electrophoresis arts will recognize that a wide range of electric potentials or field strengths may be used. In general, the electric potential applied is such as to achieve the desired EOF, which is dependent on the nature of the electrokinesis buffer and, in particular, the nature of the charged hydrophilic polymer therein. For example, fields of 10 to 1000 V/cm may be used with 200–600 V/cm being more typical. However, higher or lower fields may be employed depending on the factors mentioned above.

Polarity depends on the nature of the materials of interest and on the nature of the electrokinesis buffer. Normal polarity is to have the injection end of the capillary at a positive potential. The electroosmotic flow is normally toward the cathode. Hence, with normal polarity all positive ions and many negative ions will move away from the injection end. Generally, the "end capillary" detector will be near the cathode. The polarity may be reversed for strongly negative ions so that they move against the electroosmotic flow. When the surface of a capillary or channel is positive, the injection end is a negative (or ground) and the detection end is at the positive potential. Thus, all negative ions and many positive ions move to the detection end.

The electrodes may be strip metal electrodes formed in a stamping process or chemical etching process. The electrodes may be wires or strips either soldered or glued with epoxy and can be made of conductive materials such as platinum, gold, carbon fibers and the like. The electrodes could be deposited, coated or plated onto a section of the exterior wall of a capillary near each end of the capillary.

It is preferable for the electrodes/power supply to be connected to an electronic computer. The computer has programmed software dedicated to providing the appropriate voltages to the electrode wells. Various types of software can be provided so as to obtain the best possible results in the particular microfluidic processing conducted. The computer software that is connected to the electrodes by means of a power supply may be made interactive with an optical detection device such as ultraviolet or fluorescence spectrometer. The spectrometer can be focused singly or at various points along the medium in the channels. As the ultraviolet spectrometer reads different types of substances being moved to different portions of the medium, the information can be sent to the computer.

The microfluidic devices may be fabricated from a wide variety of materials, including glass, silica, quartz, ceramics and polymers, including elastomeric material, thermosets and thermoplastics, e.g., acrylics, and the like. The various components of the apparatus may be fabricated from the same or different materials, depending on a number of factors such as, e.g., the particular use of the device, the economic concerns, solvent compatibility, optical clarity, color, mechanical strength, dielectric properties, e.g., dielectric strength greater than 100 V/cm, and so forth. For applications where it is desired to have a disposable device, due to ease of manufacture and cost of materials, the device typically is fabricated from a plastic. For ease of detection and fabrication, the entire apparatus may be fabricated from a plastic material that is optically transparent. Particular plastics finding use include polymethyl methacrylate, polymethyl acrylate, polycarbonate, polyethylene terephthlate, polystyrene or styrene copolymers, polyesters, and the like.

Another aspect of the present invention comprises kits for processing a sample. In one embodiment a kit comprises in packaged combination (a) a microfluidic device and (b) an electrokinesis buffer, usually a powder, which provides an aqueous medium of pH about 3 to about 12 and an effective amount of at least one of positively or negatively charged polysaccharides. The kit may further comprise one or more reagents for conducting a microfluidic process. The reagents for the kits may be packaged in the same or separate containers, so that the concentration of the reagents provides for substantial optimization of the method and assay. The reagents may each be in separate containers or various reagents can be combined in one or more containers depending on the cross-reactivity and stability of the reagents. Under appropriate circumstances one or more of the reagents in the kit can be provided as a dry powder, usually lyophilized, including excipients, which on dissolution will provide for a reagent solution having the appropriate concentration for performing a method or assay in accordance with the present invention. The kit can also include additional reagents depending on the nature of the method for which the kit is used. For example, the kit may include solid phase extraction materials including paramagnetic beads and non-magnetic particles, lysis solutions, wash and elution and running buffers, biomolecular recognition elements including receptors, enzymes, antibodies and other specific binding pair members, labeling solutions, substrates, reporter molecules, sample purification materials including membranes, beads, and the like, and so forth.

EXAMPLES

The following examples are offered by way of illustration and not by way of limitation. Parts and percentages are by weight unless otherwise indicated. Temperatures are in degrees Centigrade (° C.) unless indicated otherwise. The following preparations and examples illustrate the invention but are not intended to limit its scope.

Materials

DextranT500 (Pharmacia Biotech, Piscataway, N.J., catalog # 17-0330-02)

N-(2,3-epoxypropyl)phthalimide (Sigma-Aldrich Chemical Co., Milwaukee, Wis., catalog # 15,886-0)

Epichlorohydrin (Sigma-Aldrich Chemical Co., catalog #24, 069-9)

Zinc tetrafluoroborate hydrate (Sigma-Aldrich Chemical Co., catalog #33,887-5)

Bromoacetic acid (Sigma-Aldrich Chemical Co., #25,935-7)

Ethylenediaminetetraacetic acid, EDTA (Sigma-Aldrich Chemical Co., catalog #24,072-9)

Sodium borohydride (Sigma-Aldrich Chemical Co., catalog #21,346-2)

Hydroquinone (Sigma-Aldrich Chemical Co., catalog #24, 012-5)

Ammonium hydroxide, 28–30% (VWR Scientific Products, Pittsburgh, Pa., catalog # JT9721-5)

Glycidyltrimethylammonium (Aldrich-Fluke Chemical Co., Milwaukee, Wis. catalog #50053)

Rhodamine B base, Cat.~23414-1, Sodium Fluorescein, Cat#16630-8 (both from Aldrich Chem. Co., Milwaukee, Wis.)

Sodium acetate, Cat. # S3272, Hepes ((N-[2-Hydroxyethyl] piperazine-N'-[2 ethenesulfonic acid])),Cat.# H3375,Taps (N-tris[Hydroxymethyl]methyl-3 aminopropanolsulfonic acid), Cat.# T9659, glycine, Cat.# G8898, Magnesium acetate, Cat.# M2545, Sodium ATP, Cat. # A5394, Zinc Chloride, Cat. #Z4875, Alkaline phosphatase, Cat. # P7640, DEAE dextran, Cat. # D9885 (all from Sigma Chemical Co., St. Louis, Mo.)

Human c-Src tyrosine kinase, Cat. # 14-117 (Upstate Biotechnology, Lake Placid, N.Y.)

Fluorescein diphosphate, tetraammonium salt, Cat. # F2999, amino dextran Cat. # D 9611 (both from Molecular Probe, Eugene, Oreg.)

PP2, ((4-amino-5-(4-chloro-phenyl)-7-(t-butyl)pyrazolo[3, 4-d]pyrimidine), Cat. # 529572 (CalBiochem, La Jolla, Calif.)

Cdc2 fluorescein labeled, FITC-KKAA (SEQ ID NO:1), FITC-KKKA (SEQ ID NO:2), FITC-KKKK (SEQ ID NO:3) (all from AnaSpec, San Jose, Calif.)

Ammonium Guar gum 1; (Guar gum, 2 Hydroxypropyl, 2-hydroxy-3 (Trimethylammonio)propyl Ether Chloride) was from Rhodia North American Chemicals, Cranbury, N.J.

Ammonium Guar gum 2; (Guar gum, 2 Hydroxypropyl, -3(Trimethylammonio)propyl Ether Chloride) was from Rhodia North American Chemicals.

Abbreviations g—grams h—hours min—minutes mM or mmol—millimolar ml—milliliter

M—molar $\mu$l—microliter

D.I. water—deionized water

PMMA—polymethylmethacrylate

RT—room temperature

DEAE—diethylaminoethyl dextran

PI—isoelectric point

FITC—Flurescein isothiocyanate

Example 1

Preparation of Trimethylammoniumdextrans

Two methods for the preparation of trimethylammonium-dextrans (MW 500,000 D) were employed. The first method utilized hydrolysis and needed an excess of sodium borohydride to prevent oxidation of the dextran. The second method employed the reagent zinc tetrafluoroborate hydrate and was more specific, attaching one trimethylammonium group to between six to seven dextrans.

Trimethylammoniumdextran (MW 500,000 D) Hydrolysis Method

A solution of dextran T500 (10 g) and water (30 ml) was heated to 85–90° C. (external temperature). To the solution was added in order, after dissolving, the following reagents: ethylenediaminetetraacetic acid (0.002 g, 0.007 mmol), sodium borohydride (0.002 g, 0.053 mmol), hydroquinone (0.002 g, 0.018 mmol), sodium hydroxide pellets (4.26 g, 115.50 mmol). During the course of the reaction sodium borohydride in 0.002 g portions was added to prevent oxidation of the dextran. Then, glycidyltrimethylammonium chloride (130 ml, mmol was added dropwise for 1.5 h and the reaction mixture was heated at 85–90° C. for 3 h. After cooling, the pH of the reaction mixture was adjusted to pH 11, water (500 ml) was added and the product was precipitated in methanol.

Trimethylammoniumdextran (MW 500,000 D) (1:6.3 trimethylammonium group:dextrans)

A mixture of dextran T500 (10 g) and water (30 ml) was heated at 5060° C. (internal temperature) until the dextran dissolved. Then, the solution was heated to 80° C. and zinc tetrafluoroborate hydrate (5.74 g, 15.72 mmol) was added. The reaction mixture was heated to 87° C., then glycidyltrimethylammonium chloride (130 ml, mmol) was added dropwise for 1 h. The temperature rose to 100° C. and heating at 100° C. was continued for 4 h, reduced to 70° C. for 16 h, then increased to 100° C. until the reaction mixture became clear (3 h). After cooling, the product was precipitated in methanol.

Example 2

Preparation of Aminodextrans

Two methods for the preparation of aminodextrans (MW 500,000 D) were employed. The first method using N-(2,3-epoxypropyl) phthalimide is a general scheme for attaching amine groups to dextran and is dependent upon the amount of water used in the reaction. The second method using the reagent zinc tetrafluoroborate hydrate is more specific, attaching one amine group to between six to seven dextrans.

Aminodextran (MW 500,000 D)

A solution of dextran T500 (50 g) and water (250 ml) was heated to 85–90° C. (external temperature). To the solution was added in order, after dissolving, the following reagents: sodium hydroxide pellets (22.5 g, 562.5 mmol), ethylenediaminetetraacetic acid (0.015 g, 0.05 mmol), sodium borohydride (0.015 g, 0.40 mmol), hydroquinone (0.015 g, 0.14 mmol). Then, N-(2,3-epoxypropyl)phthalimide (100 g, 492.13 mmol) was added and the reaction mixture was stirred at 85–90° C. for 2 h. After cooling, water (200 ml) was added and the product was purified and precipitated in methanol, dialyzed with membrane against water, and lyophilized to obtain a pure white solid.

$^1$H-NMR (D$_2$O, 300 MHz) 4.9–5.3 (3s, 1H), 4.8 (2, 2H), 3.5–4.3 (bm, 6H).

Aminodextran (MW 500,000 D) 1:6.3 (amino groups:dextrans)

A mixture of dextran T500 (10 g) and water (30 ml) was heated at 50–60° C. (internal temperature) until the dextran dissolved. Then, the solution was heated to 80° C. and zinc tetrafluoroborate hydrate (5.74 g, 15.72 mmol) was added. The reaction mixture was heated to 87° C., then, epichlorohydrin (70 ml, 894.95 mmol) was added dropwise for 1 h. Heating at 80° C. was continued for 6 h. After cooling, the chlorodextran intermediate was precipitated in methanol. To the dried chlorodextran was added 28–30% ammonium hydroxide solution and the solution were stirred at room temperature for 4 days. The ammonium hydroxide solution was removed in vacuo and the residue was purified and precipitated in methanol, dialyzed with membrane against water, and lyophilized to afford the pure white product.

$^1$H-NMR (D$_2$O, 300 MHz) 4.9–5.3 (3s, 1H), 4.8 (2, 2H), 3.5–4.3 (bm, 6H).

Substituted Aminodextrans (MW 500,000 D)

To chlorodextran was added the desired amine and the solution was stirred at room temperature for 4 days. The excess amine was removed in vacuo and the residue was purified and precipitated in ethanol, to afford the pure product.

Carboxymethyldextran

A mixture of dextran T500 (10 g) and water (30 ml) was heated at 50–60° C. (internal temperature) until the dextran dissolved. After cooling to room temperature, an ice-cold solution of sodium hydroxide in water (15 ml, 12.5M) was added. A solution of bromoacetic acid (8.5 g, 61.17 mmol) in ice cold water (10 ml), kept on ice, was neutralized with an ice cold solution of sodium hydroxide in water (10 ml, 5.75M), then added to the dextran solution and heated at 50° C. for 18 h. After cooling, the product was purified and precipitated in ethanol.

$^1$H-NMR (D$_2$O, 300 MHz) 5.15+4.95 (s+s, 1H), 4.8 (s, 2H), 3.5–4.3, 6H).

Example 3

Analysis of Dextrans
$^1$H NMR of Guars: Purified
Determination of Amine Density in Aminodextrans
Amine Titration A method for determining amine density in aminodextrans has been developed. The simple technique of derivatizing the aminodextran to be tested using the ATTO-TAG® CBQCA amine derivatization kit (Molecular Probes, Eugene, Oreg., catalog # A-2333) was utilized. A 0.15 mM amine concentration of 1:15 known amine density aminodextran was used as the standard. To 10 $\mu$M standard (50 $\mu$l) or 10 $\mu$M unknown aminodextran (50 $\mu$l) in phosphate buffer (200 $\mu$l) was added 10 mM CBQCA (90 $\mu$l), then 10 mM potassium cyanide (150 $\mu$l). After 10 minutes the sample absorbance at 490 nm was read using the 3010 Hitachi UV spectrophotometer, and every 10 minutes thereafter for 1 hour. Using Cricket Graph analysis the linear concentration/absorbance curves were used to determine the amine density of the unknown aminodextran.

Example 4

Procedure for Dynamic Coating and for the Determination of the EOF in Microfluidic Devices Coated in Accordance with the Present Invention The EOF was determined in a microfluidic device (manufactured from acrylate-based polymeric material in a manner similar to that described in U.S. Pat. Nos. 5,750,015, 5,126,022, 5,770,029 and 5,858,188), which had been coated dynamically with a number of positively and negatively charged polysaccharide polymers, as described below. EOF's were also determined for one plastic PMMA device and for PMMA and fused silica capillaries. The channels in the microfluidic devices and the capillaries were first treated with a 1M NaOH solution to activate and clean the surface of the device. The device was then rinsed with D.I. water. The 1M sodium hydroxide was pumped through the device or capillary for 10–60 minutes followed by pumping D.I. water for 5–15 minutes, the device is then ready for the polymer treatment. All reactions were carried out at RT.

The charged polymer was dissolved in a buffer in concentrations between 0.005 to 1%. The device channels and electrode and sample wells were typically rinsed with this buffer prior to electrophoresis for 5 to 60 minutes. The polysaccharide-containing buffer was used as the electrokinesis buffer. To compare the EOF generated by different polymers the device and capillary surface pre-treatment lasted 30 minutes prior to electrophoresis. The EOF was determined by fluorescence detection of rhodamine B base, a neutral marker at pH 7.5. The plastic device had channel dimensions of 80 $\mu$m wide and 30 $\mu$m deep. The sample was detected 0.5 cm from the injection point and the applied separation voltage was 256 V/cm. The plastic and fused silica capillaries had separation channels with a 50 $\mu$m diameters. The samples were detected 6.7 cm from the injection point and the applied separation voltages were 600 V/cm. The charged polysaccharides used for dynamic coating were synthesized or obtained from commercial sources as indicated.

The EOF was cathodal (towards the negative electrode) for the untreated surfaces and for dynamically coated carboxymethyl polysaccharide surfaces, and the EOF was anodal for dynamically coated amine functionalized polysaccharide surfaces. Table 1 lists the EOF in microfluidic devices and in capillaries dynamically coated with charged polysaccharides. The concentration of polysaccharides in the electrokinesis buffer is given.

The EOF as a Function of pH in Dynamically Coated Plastic Microfluidic Devices

A microfluidic device surface that has an EOF independent of the pH of the electrophoresis is highly desirable. Microfluidic devices with surfaces dynamically coated with positively charged polysaccharides exhibited moderate EOF fluctuation in a large pH range, as opposed to fused silica and glass devices where EOF changed by several orders of magnitude. Two examples of the microfluidic device EOF dependence of the electrokinesis buffer pH are given. The EOF was determined in plastic PMMA capillaries after surface conditioning with NaOH, D.I. water and electrokinesis buffer as previously described. The electrokinesis buffer contained 0.5% aminodextran (MW 500,000, amine/glucose ratio=1/15) in acetate or Hepes buffer (Table 2). EOF was determined in the plastic device after the same surface conditioning procedure. The electrokinesis buffer contained 0.05% ammonium guar (MW 2,000,000) in acetate, Hepes, Taps or glycine buffer dependent on pH. (Table 3). Rhodamine B base (Aldrich Chem. Co., Cat.# 23414-1) was used as EOF marker. The moderate EOF change over a large pH range facilitates prediction of analyte migration direction and magnitude in method development and potentially provides more reproducible results.

TABLE 1

Determination of electroosmotic flow (EOF) generated in PMMA assay cards, PMMA capillaries and fused silica capillaries from charged polysaccharides. Composition, molecular weight and ratio of charged groups per monosaccharide are listed.

| COMPOUND | MOLECULAR WEIGHT | RATIO Nitrogen/ monosaccharide | EOF ($10^{-5}$ cm$^2$/Vs) in PMMA assay card | EOF ($10^{-5}$ cm$^2$/Vs) in PMMA capillary | EOF ($10^{-5}$ cm$^2$/Vs) in fused silica capillary |
|---|---|---|---|---|---|
| Positively Charged Dextrans 1% | | | | | |
| Aminodextran | 500000 | 1:15 | 3 | 7 | |
| Aminodextran | 65000 | 1:22 | | 1 | |

TABLE 1-continued

Determination of electroosmotic flow (EOF) generated in PMMA assay cards, PMMA capillaries and fused silica capillaries from charged polysaccharides. Composition, molecular weight and ratio of charged groups per monosaccharide are listed.

| COMPOUND | MOLECULAR WEIGHT | RATIO Nitrogen/ monosaccharide | EOF ($10^{-5}$ cm$^2$/Vs) in PMMA assay card | EOF ($10^{-5}$ cm$^2$/Vs) in PMMA capillary | EOF ($10^{-5}$ cm$^2$/Vs) in fused silica capillary |
|---|---|---|---|---|---|
| Aminodextran | 500000 | 1:>15 | | 4 | |
| Aminodextran | 500000 | 1:15 | | 6 | |
| Aminodextran | 500000 | 1:9 | | 13 | |
| Aminodextran | 500000 | 1:5 | 5 | 12 | 11 |
| Aminodextran | 500000 | 1:17 | 2 | | |
| Ethanolaminodextran | 500000 | | 2 | | |
| Diethylenetriaminodextran | 500000 | | 0 | | |
| Dimethylaminodextran | 500000 | | | | |
| Diethylaminodextran | 500000 | | | | |
| Methylaminodextran | 500000 | | | | |
| Negatively Charged Dextrans 0.5% | | | | | |
| Carboxymethyldextran | 2000000 | | | −20 | |
| Positively charged Charged Dextrans 0.5% | | | | | |
| Ammonium Dextran | 500000 | 1:5 | | 6 | |
| Ammonium Dextran | 500000 | 1:5 | 2 | 5.3 | |
| Ammonium Dextran, NaOH method | 500000 | 1:1 | 13 | | |
| Ammonium Dextran, Zn method | 500000 | | 5 | | |
| Commercial products | | | | | |
| DEAE dextran, Sigma 0.1% | 500000 | 1:3 | 9 | 14 | 14 |
| Ammonium guar gum 1, Rhodia 0.1% | 2000000 | 1:3 | 9 | 14 | 15 |
| Ammonium guar gum 2, Rhodia 0.1% | 2000000 | 1:2 | 14 | | |
| Control No Polymer | | | −5 | −9 | −40 |

TABLE 2

EOF as function of pH determined in PMMA capillaries dynamically coated with aminodextran. The EOF was measured using the Beckman PACE Instrument with Rhodamine B Base as a neutral marker. The electrokinesis buffer contained 0.5% aminodextran (1:15) as surface modifier.

| pH | EOF ($10^{-5}$ cm$^2$/Vs) |
|---|---|
| 5.2 | 8.5 |
| 6.7 | 6.9 |
| 7.0 | 6.4 |
| 7.5 | 6.6 |
| 7.8 | 5.6. |
| 8.2 | 5.5 |

TABLE 3

EOF as function of pH determined in PMMA assay card dynamically coated with ammonium guargum. The EOF was measured on a PMMA assay card connected to a computer controlled power supply. A fluorescence detector traced the neutral marker Rhodamine B Base. The electrokinesis buffer contained 0.05% ammonium guar (1:3) as surface modifier. The relative current is included for the buffers.

| pH | EOF ($10^{-5}$ cm$^2$/Vs) | I μA | Buffer |
|---|---|---|---|
| 4.6 | 6.8 | 13 | 15 mM NaAc |
| 5.4 | 7.5 | 9 | 15 mM NaAc |
| 6.4 | 10.5 | 3 | 25 mM Hepes |
| 7.5 | 9.8 | 7 | 25 mM Hepes |
| 8.5 | 7.5 | 10 | 25 mM Taps |
| 9.4 | 8.4 | 8 | 10 mM glycine |

Example 5

Figure 3:
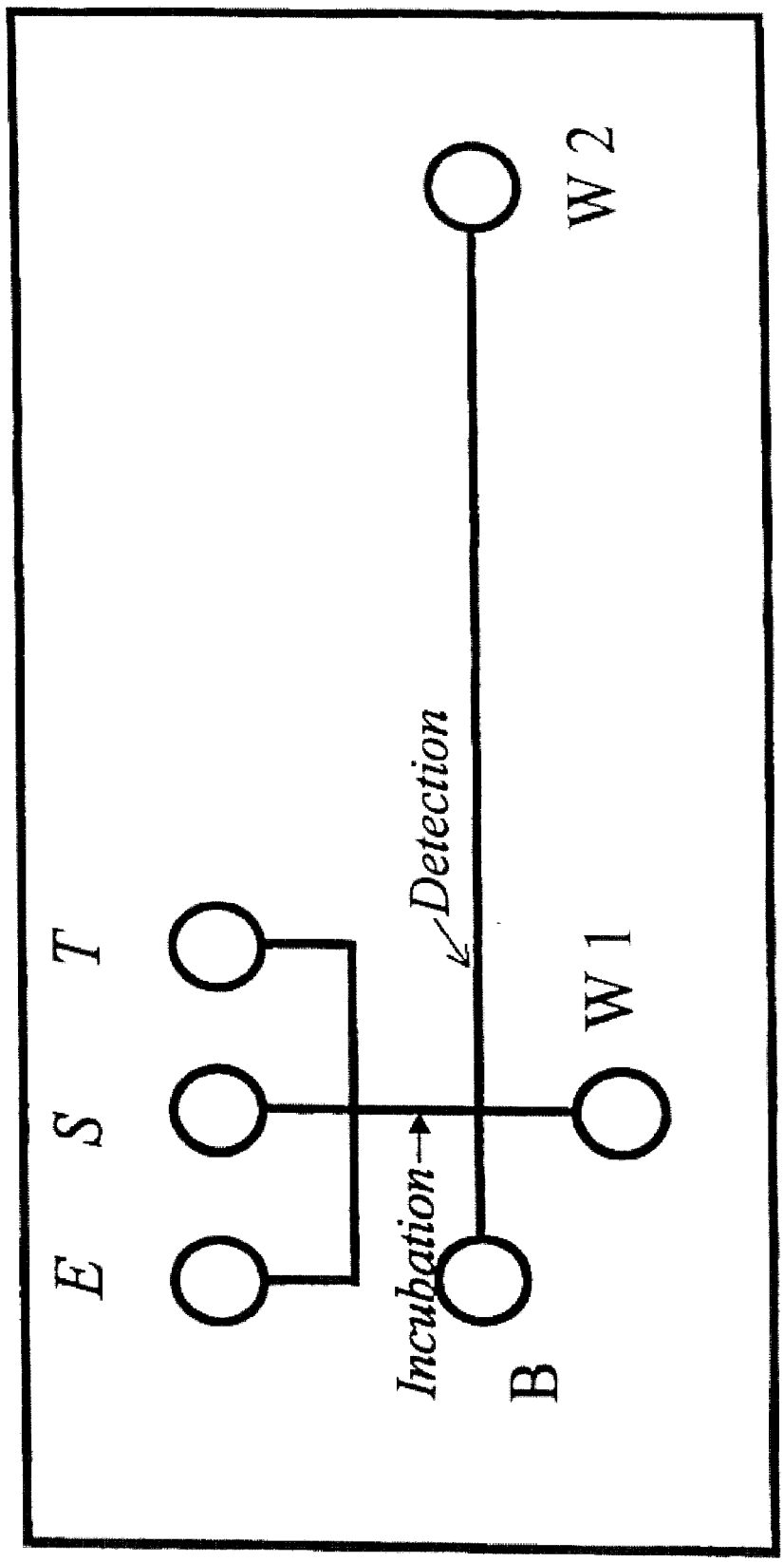
FIG. 3 is a schematic diagram of a microfluidic assay card used to carry out experiments in accordance with the present invention.

Typical Microfluidic Assay Card with in Card Reagent Mixing, Incubation and Detection Microchannels are connected to sample and buffer wells marked E, S, T, B, W1 and W2 in FIG. 3. The channels and wells B and W1 and W2 were filled with electrokinesis buffer. Wells E, S and T are filled with assay reagents. Electrodes are placed in all wells. Voltage is applied so that reagents from wells E, S and T migrate toward W1. Mixing and incubation occurred in the common channel. By changing the voltages a small plug of mixed and incubated assay mixture was diverted into the channel connecting wells B and W2. The analytes separated in this channel and were detected by on line fluorescent detection. The microfluidic cards used in the examples herein were prepared from an acrylate-based polymeric material in a manner similar to that described in U.S. Pat. Nos. 5,750,015, 5,126,022, 5,770,029 and 5,858,188.

Example 6

Transport and Separation of Positively and Negatively Charged Proteins in Dynamically Coated Plastic PMMA Capillaries The potential to transport both positively and negatively charged proteins in a microfluidic device with good recovery is vital for a large number of on-chip assays that involve mixing of protein reagents (such as enzymes) with other assay reagents. The transport of the proteins has to be done under optimal assay reaction conditions and pH. Thus, the proteins to be transported could be both positively or negatively charged depending on the optimal assay pH. The most common method to assure good protein recovery in protein separation and transport has been to have neutral hydrophilic channel surface (Hjerten, J. Chrom. (1985) 347:191–198) or to perform the protein transport and separation in a separation channel where the channel surface has the same net charge as the protein and is thus repelled from the surface Lauer, et al., *Anal. Chem.* (1986) 15:166–170. These strategies, however, can not be applied when transport by EOF is required and reactants of opposite charges need to be mixed. Positively charged polysaccharides as dynamic surface coating can transport both negatively and positively charged proteins in one run.

Figure 2:
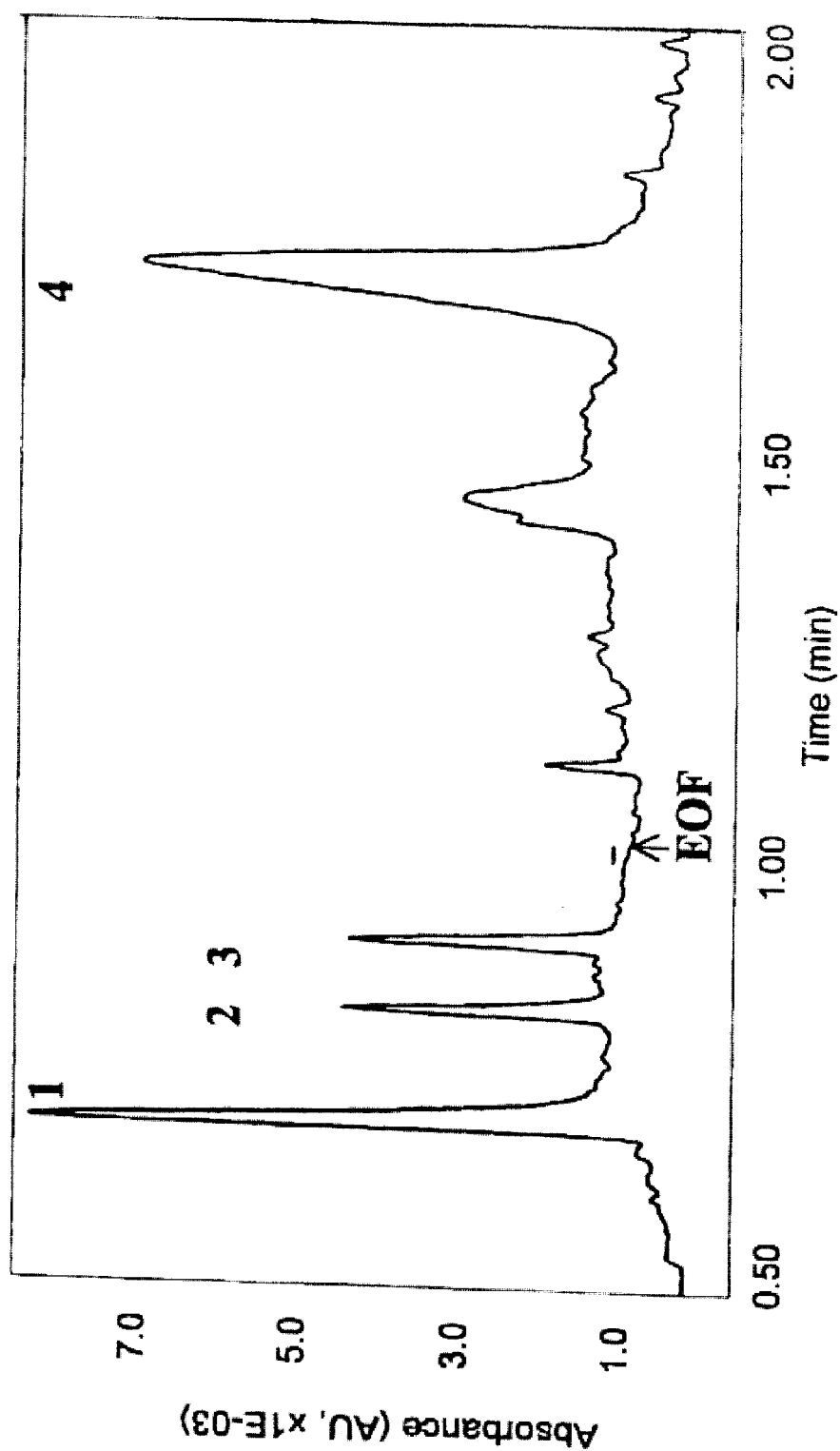
FIG. 2 is a graph depicting results of experiments carried out in accordance with the present invention.

As an example, a number of proteins with isoelectric point from 4.5–9.3 were separated with good efficiencies in one run (FIG. 2). The pH of the electrokinesis buffer was 7.5. At this pH lactalbumin (1) pI 4.5, carbonic anhydrase (2) pI 5.9 and myoglobin (3) pI 7.2 were negatively charged and trypsinogen (4) pI 9.3 was positively charged. Plastic PMMA capillaries were pretreated with NaOH, D.I. water and electrokinesis buffer as described before. The PMMA capillary had an I.D. of 50 μm. The electrokinesis buffer contained 0.05% ammonium guar gum and 25 mM Hepes, pH 7.5. The separation was performed at 600 V/cm and detection was by UV (280 nm) at a separation distance of 6.7 cm (FIG. 3). The efficiency of the protein peaks indicated that the protein recovery was good.

Example 7

Dynamically Coated Microfluidic Assay Cards Used for Enzymatic Assays. Transport and Mixing of a Positively Charged Enzyme and a Negatively Charged Substrate.

Figure 10:
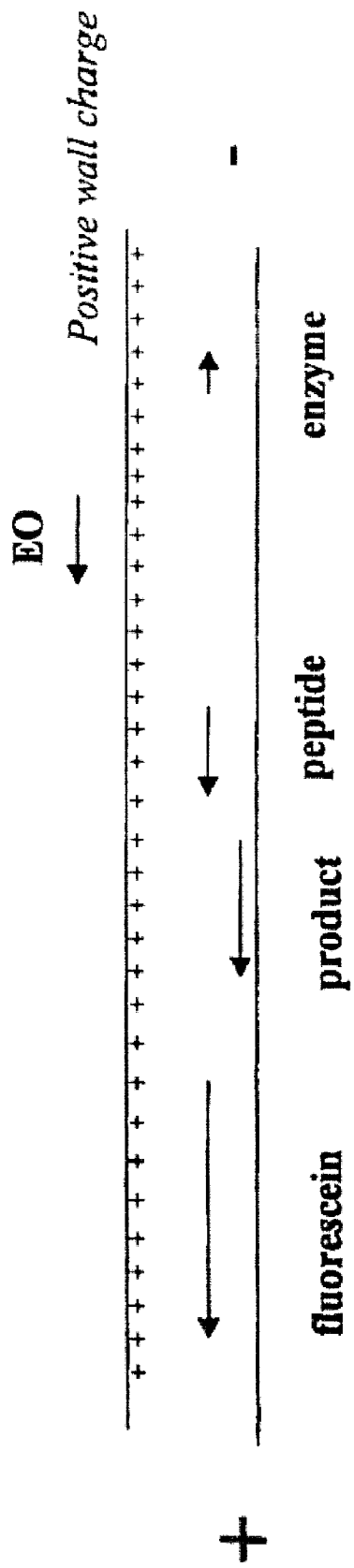
FIG. 10 is a schematic diagram depicting electroosmotic flow in accordance with the present invention.

In this example an enzymatic reaction was performed by on-card mixing. The enzyme, src tyrosine kinase, has a pH optimum at 7.5 at which pH the transport, mixing incubation and separation occurred. The src tyrosine kinase (Upstate Biotechnology, Lake Placid, N.Y., Cat. # 14–117) had a pI of 9.0 and, thus, was positively charged at pH 7.5. The substrate was the cdc2 peptide, which was fluorescein labeled and obtained from AnaSpec Inc., San Jose, Calif. The enzyme phosphorylates the peptide and the assay is based on the separation and detection of the phosphorylated product and the peptide substrate, which are both negatively charged at pH 7.5. FIG. 10 shows the relative electrophoretic mobilities and EOF utilizing the kinase assay reagents in assay cards with an electrokinesis buffer containing ammonium polysaccharide.

Figure 5:
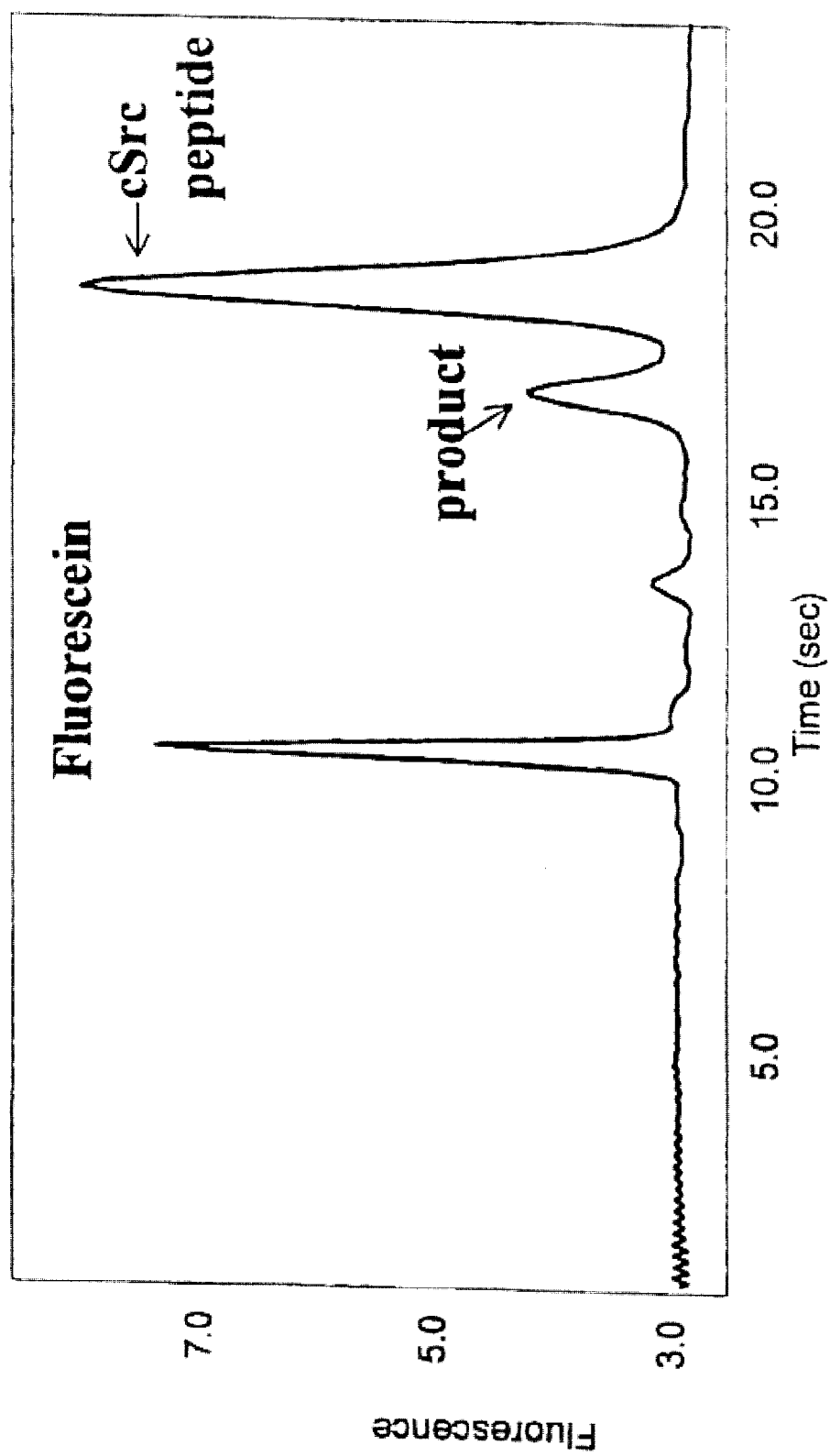
FIG. 5 is a graph depicting results of experiments carried out in accordance with the present invention.

A plastic (PMMA) assay card (FIG. 3) was pretreated with a NaOH solution to activate and clean the surface as described above. The card was then rinsed with D.I. water and filled and rinsed with a buffer of 0.05% ammonium guar (FIG. 4) in 25 mM Hepes, pH 7.5 for 30 minutes. Another card had, as surface modifier, polymers a mixture of 1% amino dextran and 0.005% DEAE dextran (FIG. 5). The electrokinesis buffer also contained sodium ATP and Mg acetate needed for the enzymatic reaction. The Src tyrosine kinase, diluted in the electrokinesis buffer to 150 ng/mL, was added to well E. The peptide substrate, diluted in the electrokinesis buffer to 100 μM, with the internal marker fluorescein was added to well S. All other wells were filled with electrokinesis buffer. Voltage was applied so that equal volumes of enzyme and substrate were mixed. The assay steps are described above with respect to FIG. 3. The separation of the injected assay mixture was done at 250 V/cm and the detection point was 0.5 cm from the injection point. The presence of the phosphorylated product indicated that enzyme and the peptide substrate were contacted. The reproducibility of mixing and transport is evident by comparing the separation of four consecutive assays (FIG. 4). These results compare well with in-well incubation; thus, the enzyme was transported in the dynamically coated chip and there was no apparent loss of enzyme. The result was low reagent consumption with on chip mixing.

Figure 6:
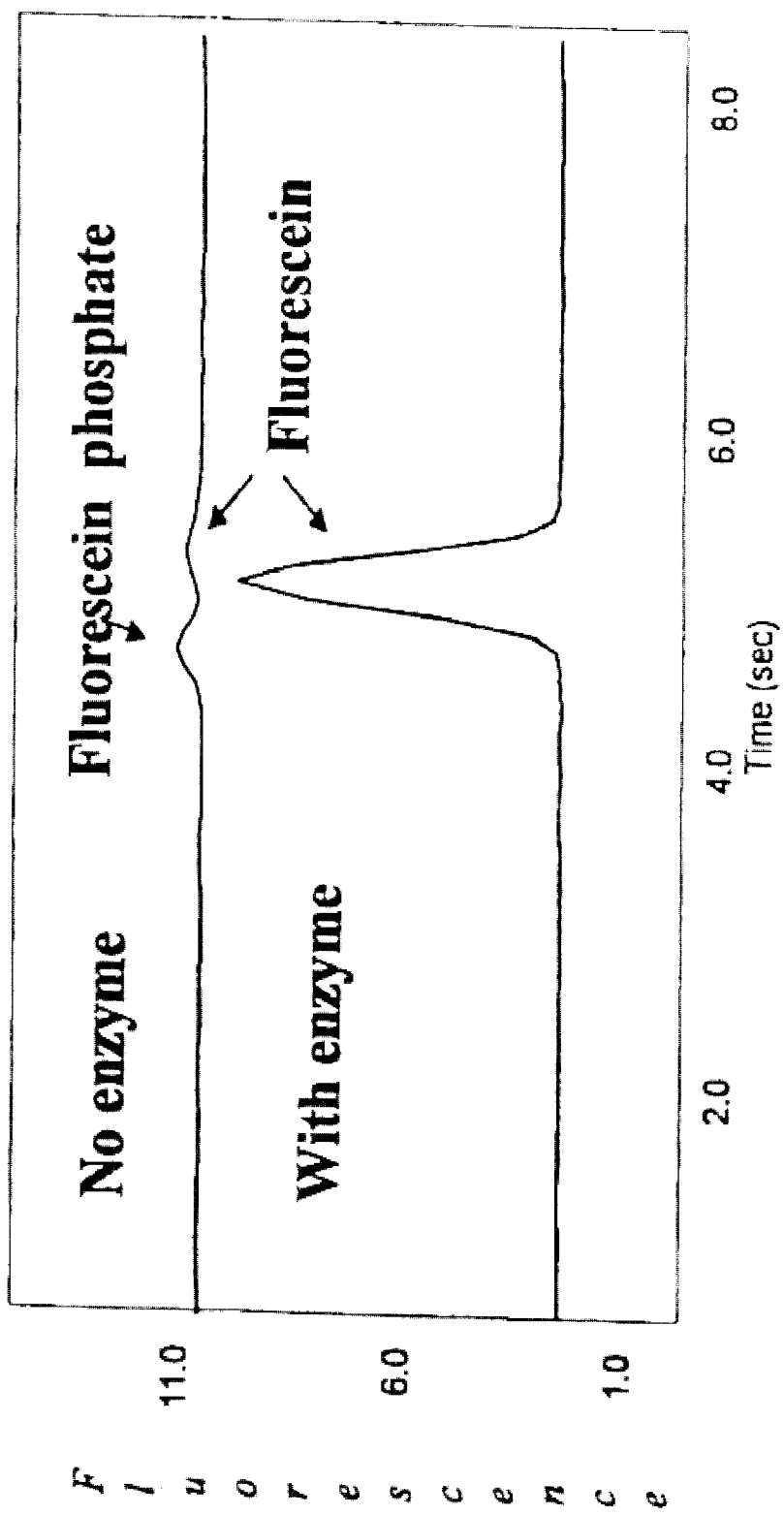
FIG. 6 is a graph depicting results of experiments carried out in accordance with the present invention.

Dynamically Coated Microfluidic Assay Cards Used for Enzymatic Assays. Transport and Mixing of a Negative Charged Enzyme and a Negatively Charged Substrate Another example of protein transport is described here to show that proteins of opposite net charge to the dynamically crated channel surface in the assay card can be transported and mixed with assay reagents. In the enzymatic assay with alkaline phosphatase and with fluorescein diphosphate as substrate, alkaline phosphatase (pI=4–5) and the substrate had a net negative charges at pH 9, at which the assay was run. The reaction product was fluorescein. Except for the electrokinesis buffer, which was 0.05% ammonium guar, 10-mM glycine, Zinc chloride and magnesium acetate, pH 9, the assay was run in the manner described above with respect to FIGS. 3–5. The presence of fluorescein in the assay mixture confirmed the enzyme transport (FIG. 6) in the assay card. A control separation of mixing the same assay reagent with buffer from well E confirmed the enzyme transport.

Figure 7:
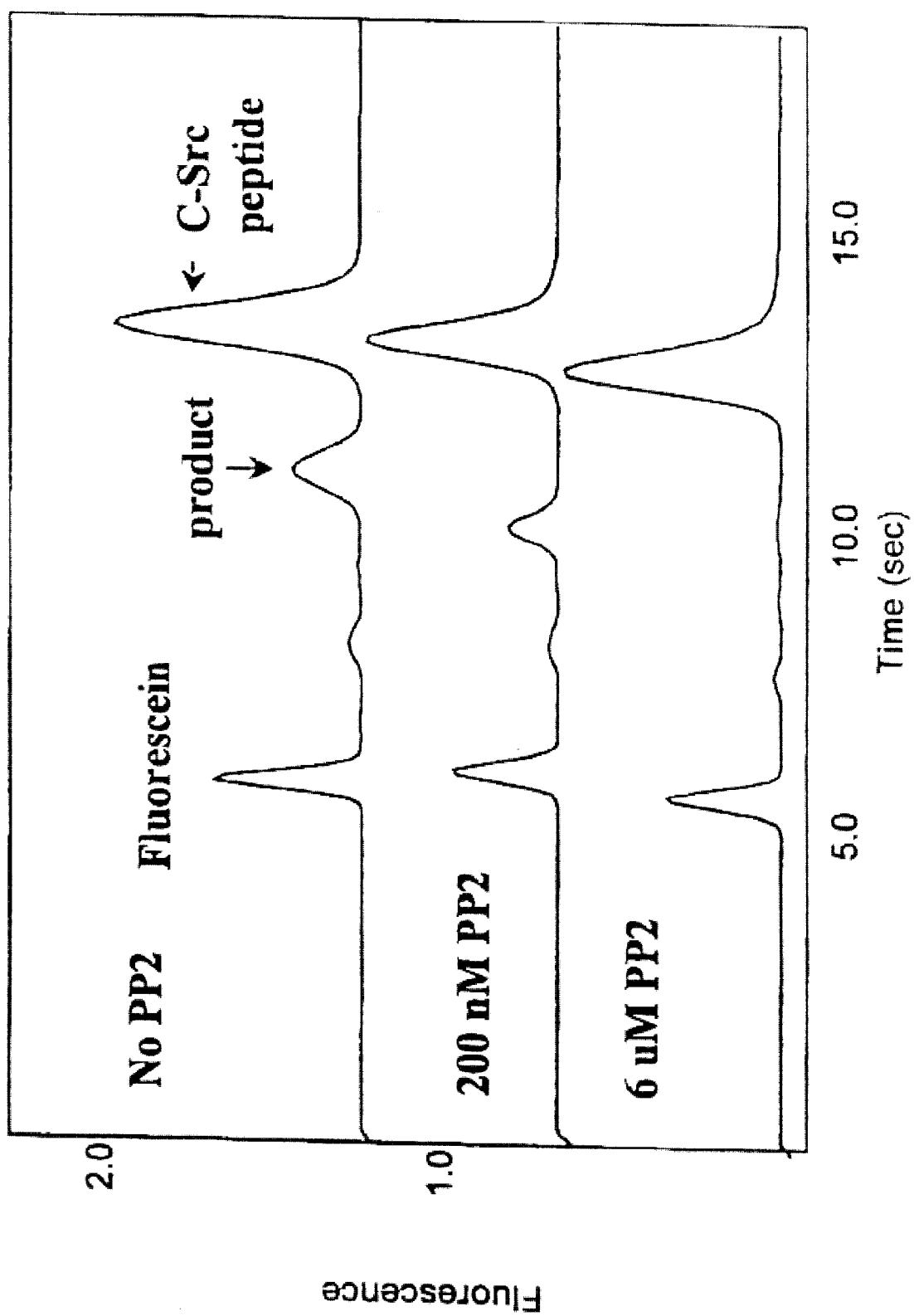
FIG. 7 is a graph depicting results of experiments carried out in accordance with the present invention.

Dynamically Coated Microfluidic Assay Cards Used for Enzymatic Assays with Hydrophobic Enzyme Inhibitor This example shows that hydrophobic compounds were transported and mixed in microfluidic assay cards that were dynamically coated with charged hydrophilic polymers. The compound chosen as an example was the potent src tyrosine kinase inhibitor PP2, ((4-amino-5-(4-chloro-phenyl)-7-(tbutyl)pyrazolo[3,4d]pyrimidine (CalBiochem, La Jolla, Calif., Cat.# 529572). The conditions for dynamic coating and assay conditions were the same as described in previous examples with the exception that the T well (FIG. 3) contained the PP2 sample and there was a three way mixing with equal volumes from wells E, S and T. The PP2 sample was dissolved in DMSO and diluted in the electrokinesis buffer containing 1% DMSO. A control with buffer (no PP2) in well T and assays with 200 nM and 6 μM PP2 in well T were performed (FIG. 7). The reduction in the product peak with increasing PP2 concentration confirmed that PP2 was transported and mixed with the assay reagents, which resulted in decreased enzyme activity. This confirmed that hydrophobic molecules were transported electrophoretically in a surface coated plastic device.

Dynamically Coated Microfluidic Assay Cards Used for Enzymatic Assays with Hydrophobic Enzyme Inhibitor. Determination of IC 50 values The dynamically coated assay card, prepared as described above, was used to determine IC 50 for the hydrophobic kinase inhibitor PP2. The measured IC 50 value was 800 nM, which compares favorably with the $IC_{50}$ value reported in the literature.

Figure 8:
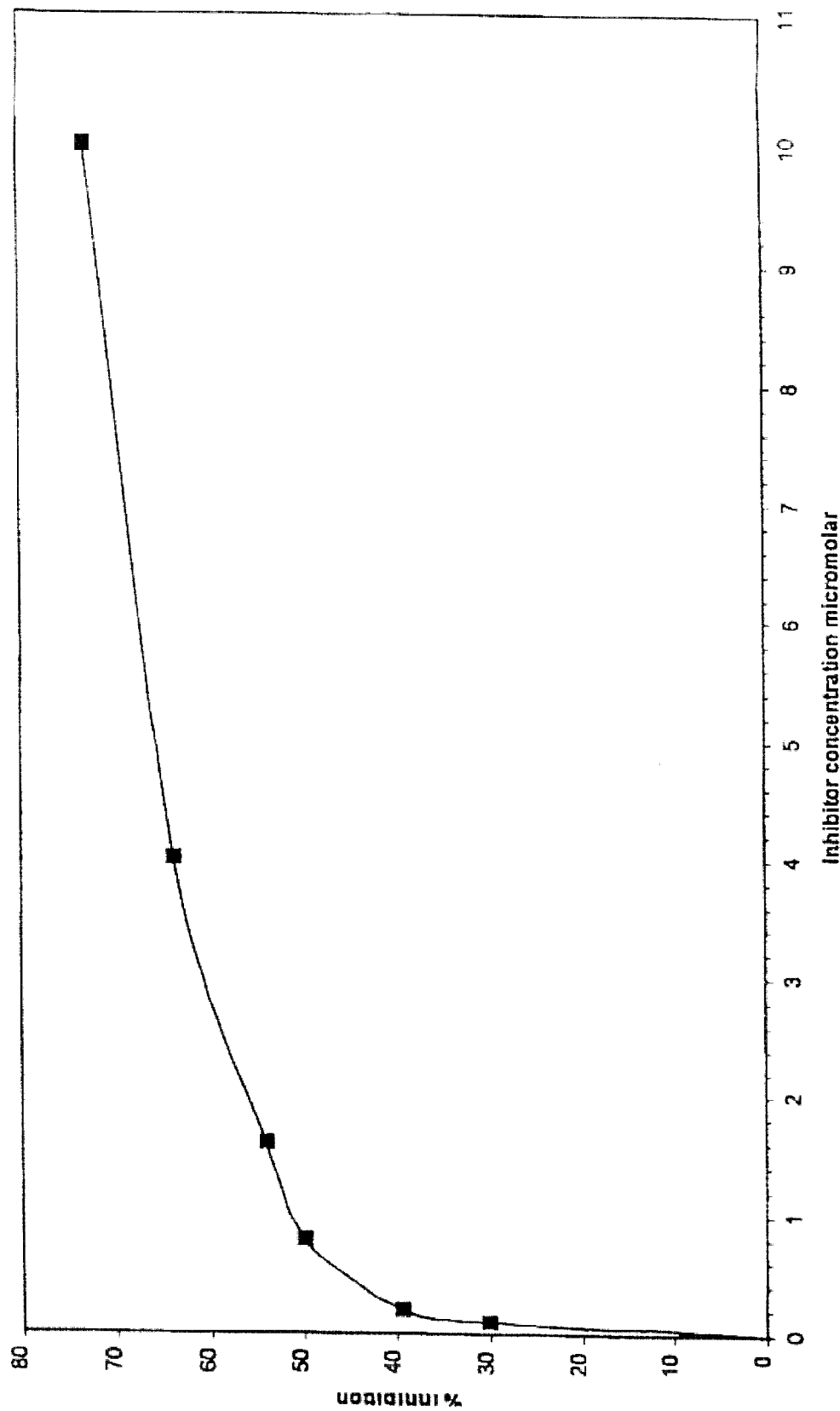
FIG. 8 is a graph depicting results of experiments carried out in accordance with the present invention.

The results are summarized in FIG. 8.

Example 8

Transport and Separation of Positively and Negatively Charged Peptides in a Dynamically Coated Chip This example demonstrated the magnitude of compounds that can be transported in one direction by using charged hydrophilic polymers to dynamically coat microfluidic channels. The coating procedure and the separation conditions were the same as described previously. The surface modifying polymer was 0.05% ammonium guar. Three FITC labeled peptides (obtained from AnaSpec, San Jose, Calif.), which differed by one charge from each other (FITC-KKAA, FITC-KKKA and FITC-KKKK), were separated and detected 0.5 cm from the injection point on the anodal side. FITC-KKAA is negatively charged and the other peptides are positive charged as determined by the migration time relative to EOF. FITC-KKKA and FITC-KKKK migrated electrophoretically against the EOF. The net charge of FITC-KKKK was greater than +1.

Figure 9:
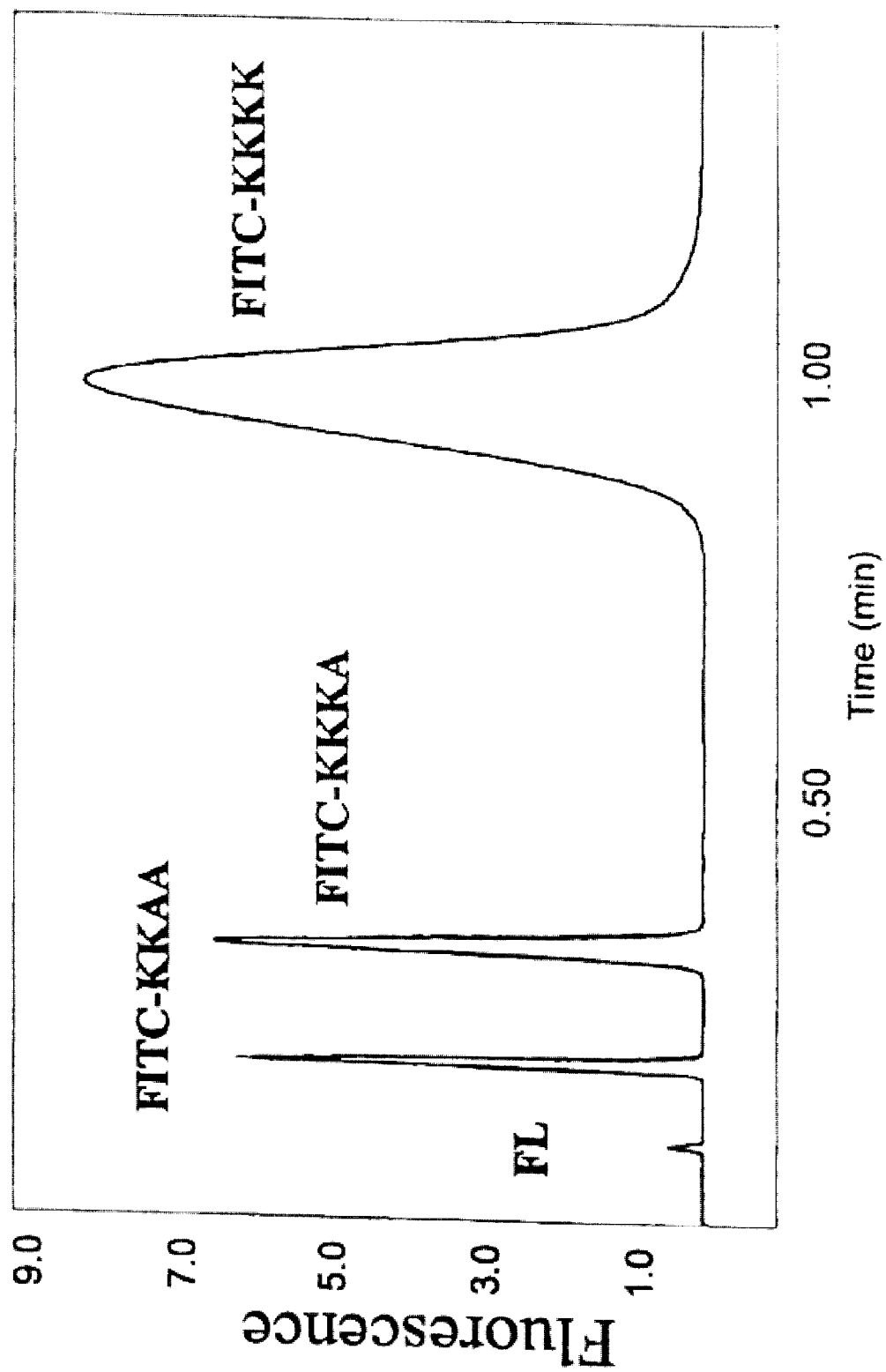
FIG. 9 is a graph depicting results of experiments carried out in accordance with the present invention.

The results are summarized in FIG. 9. This example demonstrated that a great number of positively charged compounds could be transported and mixed with assay compounds of interest. No limits to transporting negatively charged compounds were observed.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent those of ordinary skill in the art in light of the teachings of this invention that certain changes and modifications may be made thereto without departing from the spirit or scope of the appended claims.

What is claimed is:

1. A method for transporting a liquid containing at least two chemical components in a selected direction in a channel of a microfluidic system, by electrokinesis, wherein said at least two chemical components include a protein having one charge at a selected buffer pH and another component having the opposite charge at the same pH, said method comprising (a) selecting a microfluidic system having a channel formed of an acrylic-based polymer;

(b) exposing the walls of the channel to a solution containing 0.0015% to 5% weight percent of a charged hydrophilic amine polymer, wherein charges on said charged hydrophilic polymer are randomly distributed;

(c) after said exposing, filling the channel with a solution containing the at least two chemical components at the selected pH; and (d) applying a voltage from one point along said channel to a different point along said channel whereby the differently charged chemical components are transported in said selected direction along said channel.

2. The method of claim 1 wherein said said solution contains between about 0.02 to 0.5% weight percent of the polymer.

3. The method according to claim 1 wherein said hydrophilic polymer is a polyether substituted with amino groups as said charges.

4. The method according to claim 1 wherein said hydrophilic amine polymer is an amine-substituted polysaccharide.

5. The method according to claim 1 wherein said channel is formed of polymethyl methacrylate.

6. The method of claim 1, for use in electrokinetically separating a mixture of proteins, peptides, and/or polypeptides having both positive and negative charges, at a selected electrophoresis buffer pH, wherein said channel is a capillary electrophoresis channel containing an electrophoretic separation medium.

7. The method of claim 1, for use in performing an assay, said assay involving an enzyme having one electrophoretic mobility at a selected buffer pH, contained in one reservoir in the system, and a reagent having a different electrophoretic mobility at the pH, contained in a second reservoir in the system, where the two reservoirs are connected by said channel, said method comprising:

mixing the two reagents, wherein said exposing includes moving polymer from each of the two reservoirs through said channel, and said applying includes applying a same-polarity voltage across each reservoir and said channel, at the selected pH, to cause the two reagents to mix in the common channel.

* * * * *

UNITED STATES PATENT AND TRADEMARK OFFICE
CERTIFICATE OF CORRECTION

PATENT NO. : 6,306,273 B1
DATED : October 23, 2001
INVENTOR(S) : Wainright et al.

Page 1 of 1

It is certified that error appears in the above-identified patent and that said Letters Patent is hereby corrected as shown below:

<u>Title page,</u>
Under "OTHER PUBLICATIONS", line 1, "Aminodextrari" should be
-- Aminodextran --.

<u>Claim 2,</u>
Line 1, delete the second "said".

Signed and Sealed this

Ninth Day of April, 2002

Attest:

JAMES E. ROGAN
*Attesting Officer*     *Director of the United States Patent and Trademark Office*